(12) United States Patent
Chang

(10) Patent No.: US 7,052,908 B2
(45) Date of Patent: May 30, 2006

(54) ANDROGEN RECEPTOR COACTIVATORS

(75) Inventor: Chawnshang Chang, Pittsford, NY (US)

(73) Assignee: University of Rochester, Rochester, NY (US)

(*) Notice: Subject to any disclaimer, the term of this patent is extended or adjusted under 35 U.S.C. 154(b) by 42 days.

(21) Appl. No.: 10/442,754

(22) Filed: May 20, 2003

(65) Prior Publication Data

Related U.S. Application Data

(63) Continuation of application No. 09/354,221, filed on Jul. 15, 1999, now Pat. No. 6,699,714.

(60) Provisional application No. 60/093,239, filed on Jul. 17, 1998, provisional application No. 60/100,243, filed on Sep. 14, 1998.

(51) Int. Cl.
- C12N 5/00 (2006.01)
- C12N 5/12 (2006.01)
- C12P 21/06 (2006.01)

(52) U.S. Cl. ............. 435/325; 435/69.1; 435/320.1; 536/23.5; 530/350

(58) Field of Classification Search ........... 435/69.1, 435/320.1; 536/23.1, 23.5; 53/350
See application file for complete search history.

(56) References Cited

U.S. PATENT DOCUMENTS

| | | | |
|---|---|---|---|
| 5,208,263 A | 5/1993 | Liao et al. |
| 5,674,703 A | 10/1997 | Woo et al. |
| 5,677,336 A | 10/1997 | Jones et al. |
| 5,789,170 A | 8/1998 | Chang et al. |

FOREIGN PATENT DOCUMENTS

WO  WO 97/44490 A  11/1997

OTHER PUBLICATIONS

Anderson et al. Retinoblastoma protein in human breast carcinoma: immunohistochemical study using a new monoclonal antibody effective on routinely processed tissues. J Pathol. Sep. 1996;180(1):65-70.

Anzick et al. AIB1, a steroid receptor coactivator amplified in breast and ovarian cancer. Science. Aug. 15, 1997;277(5328):965-8.

Beddow et al. The Ran/TC4 GTPase-binding domain: identification by expression cloning and characterization of a conserved sequence motif. Proc Natl Acad Sci U S A. Apr. 11, 1995;92(8):3328-32.

Blake et al. The sequences of the human and mouse c-cbl proto-oncogenes show v-cbl was generated by a large truncation encompassing a proline-rich domain and a leucine zipper-like motif. Oncogene. Apr. 1991;6(4):653-7.

Bookstein et al. Promoter deletion and loss of retinoblastoma gene expression in human prostate carcinoma. Proc Natl Acad Sci U S A. Oct. 1990;87(19):7762-6.

Bookstein et al. Suppression of tumorigenicity of human prostate carcinoma cells by replacing a mutated RB gene. Science. Feb. 9, 1990;247(4943):712-5.

Borden et al. The solution structure of the RING finger domain form the acute promyelocytic leukaemia proto-oncoprotein PML. EMBO J. Apr. 3, 1995;14(7):1532-41.

Brooks et al. Allelic loss of the retinoblastoma gene in primary human prostatic adenocarcinomas. Prostate. Jan. 1995;26(1):35-9.

Cardoso et al. Specific interaction between the XNP/ATR-X gene product and the SET domain of the human EZH2 protein. Hum Mol Genet. Apr. 1998;7(4):679-84.

Chamberlain et al. The length and location of CAG trinucleotide repeats in the androgen receptor N-terminal domain affect transactivation function. Nucleic Acids Res. Aug. 11, 1994;22(15):3181-6.

Chang et al. Suppression of Delta(5)-androstenediol-induced androgen receptor transactivation by selective steroids in human prostate cancer cells. Proc Natl Acad Sci U S A. Sep. 28, 1999;(20):11173-7.

Chen et al. Phosphorylation of the retinoblastoma gene product is modulated during the cell cycle and cellular differentiation. Cell. Sep. 22, 1989;58(6):1193-8.

Chen et al. Retinoblastoma protein directly interacts with and activates the transcription factor NF-IL6. Proc Natl Acad Sci U S A. Jan. 9, 1996;93(1):465-9.

Crawford, Challenges in the management of prostate cancer. Br J Urol. Nov. 1992;70 Suppl 1:33-8.

Dowdy et al. Physical interaction of the retinoblastoma protein with human D cyclins. Cell. May 7, 1993;73(3):499-511.

Dynlacht et al. Isolation of coactivators associated with the TATA-binding protein that mediate transcriptional activation. Cell. Aug. 9, 1991;66(3):563-76.

Fujimoto et al. Cloning and characterization of androgen receptor coactivator, ARA55, in human prostate. J Biol Chem. Mar. 19, 1999;274(12):8316-21.

Gaddipati et al. Frequent detection of codon 877 mutation in the androgen receptor gene in advanced prostate cancers. Cancer Res. Jun. 1, 1994;54(11):2861-4.

(Continued)

Primary Examiner—Olga N. Chernyshev
(74) Attorney, Agent, or Firm—Needle & Rosenberg, PC

(57) ABSTRACT

Disclosed are androgen receptor-associated proteins, designated ARA24, ARA54, ARA55, and Rb, that have been demonstrated to interact with the androgen receptor to alter levels of androgen receptor-mediated transcriptional activation. Certain of these proteins interact with the androgen receptor in an androgen-dependent manner, whereas certain proteins may induce transcriptional activation in the presence of other ligands, such as E2 or HF. Also disclosed is a method of detecting androgenic or antiandrogenic activity using these proteins in a mammalian two-hybrid transient transfection assay.

16 Claims, No Drawings

OTHER PUBLICATIONS

Gregory et al. Androgen receptor expression in androgen-independent prostate cancer is associated with increased expression of androgen-regulated genes. Cancer Res. Dec. 15, 1998;58(24):5718-24.

Gregory, C.W. et al. A mechanism for androgen receptor-mediated prostate cancer recurrence after androgen deprivation therapy. *Cancer Res* 61, 4315-4319. (2001).

Gu et al. The t(4;11) chromosome translocation of human acute leukemias fuses the ALL-1 gene, related to Drosophila trithorax, to the AF-4 gene. Cell. Nov. 13, 1992;71(4):701-8.

Han et al., Hormone status selects for spontaneous somatic androgen receptor variants that demonstrate specific ligand and cofactor dependent activities in autochthonous prostate cancer. J Biol Chem. Apr. 6, 2001;276(14):11204-13.

Heery et al. A signature motif in transcriptional co-activators mediates binding to nuclear receptors. Nature. Jun. 12, 1997;387(6634):733-6.

Hillier et al. Wash U-Merck EST Project 1997. EMBL ACC No.: AA448471 (Jun. 10, 1997).

Hsiao et al. The linkage of Kennedy's neuron disease to ARA24, the first identified androgen receptor polyglutamine region-associated coactivator. J Biol Chem. Jul. 16, 1999;274(29):20229-34.

Hsiao, P., and Chang, C. Isolation and characterization of ARA160 as the first androgen receptor N-terminal-associated coactivator in human prostate cells. J Biol Chem. Aug. 6, 1999;274(32):22373-9.

Ishida et al. Cloning and chromosome mapping of the human Mel-18 gene which encodes a DNA-binding protein with a new 'RING-finger' motif. Gene. Jul. 30, 1993;129(2):249-55.

Kaelin et al. Identification of cellular proteins that can interact specifically with the T/E1A-binding region of the retinoblastoma gene product. Cell. Feb. 8, 1991;64(3):521-32.

Kang et al. Cloning and characterization of human prostate coactivator ARA54, a novel protein that associates with the androgen receptor. J Biol Chem. Mar. 26, 1999;274(13):8570-6.

Kang et al. From transforming growth factor-beta signaling to androgen action: identification of Smad3 as an androgen receptor coregulator in prostate cancer cells. Proc Natl Acad Sci U S A. Mar. 13, 2001;98(6):3018-23.

Kemppainen et al. Androgen receptor phosphorylation, turnover, nuclear transport, and transcriptional activation. Specificity for steroids and antihormones. J Biol Chem. Jan. 15, 1992;267(2):968-74.

Kokontis et al. Expression and function of normal and LNCaP androgen receptors in androgen-insensitive human prostatic cancer cells. Altered hormone and antihormone specificity in gene transactivation. Receptor. 1991;1(4):271-9.

Kranenburg et al. Cyclin-dependent kinases and pRb: regulators of the proliferation-differentiation switch. FEBS Lett. Jun. 26, 1995;367(2):103-6.

La Spada et al. Androgen receptor gene mutations in X-linked spinal and bulbar muscular atrophy. Nature. Jul. 4, 1991;352(6330):77-9.

Laemmli, Cleavage of structural proteins during the assembly of the head of bacteriophage T4. Nature. Aug. 15, 1970;227(259):680-5.

Lee et al. Convergence of two repressors through heterodimer formation of androgen receptor and testicular orphan receptor-4: a unique signaling pathway in the steroid receptor superfamily. Proc Natl Acad Sci U S A. Dec. 21, 1999;96(26):14724-9.

Lee et al. Two classes of proteins dependent on either the presence or absence of thyroid hormone for interaction with the thyroid hormone receptor. Mol Endocrinol. Feb. 1995;9(2):243-54.

Lovering et al. Identification and preliminary characterization of a protein motif related to the zinc finger. Proc Natl Acad Sci U S A. Mar. 15, 1993;90(6):2112-6.

Ludlow et al. Specific enzymatic dephosphorylation of the retinoblastoma protein. Mol Cell Biol. Jan. 1993;13(1):367-72.

McPhaul et al. Genetic basis of endocrine disease. 4. The spectrum of mutations in the androgen receptor gene that causes androgen resistance. J Clin Endocrinol Metab. Jan. 1993;76(1):17-23.

Mihara et al. Cell cycle-dependent regulation of phosphorylation of the human retinoblastoma gene product. Science. Dec. 8, 1989;246(4935):1300-3.

Miki et al. A strong candidate for the breast and ovarian cancer susceptibility gene BRCA1. Science. Oct. 7, 1994;266(5182):66-71.

Mitchell et al. Resveratrol inhibits the expression and function of the androgen receptor in LNCaP prostate cancer cells. Cancer Res. Dec. 1, 1999;59(23):5892-5.

Miyamoto and Chang, Antiandrogens fail to block androstenedione-mediated mutated androgen receptor transactivation in human prostate cancer cells. Int J Urol. Jan. 2000;7(1):32-4.

Miyamoto et al. Delta5-androstenediol is a natural hormone with androgenic activity in human prostate cancer cells. Proc Natl Acad Sci U S A. Sep. 15, 1998;95(19):11083-8.

Miyamoto et al. Promotion of agonist activity of antiandrogens by the androgen receptor coactivator, ARA70, in human prostate cancer DU145 cells. *Proc. Natl. Acad. Sci. USA* 95:7379-7384 (Jun. 1998).

Mizokami and Chang, Induction of translation by the 5'-untranslated region of human androgen receptor mRNA. J Biol Chem. Oct. 14, 1994;269(41):25655-9.

Mizokami et al. Identification of 3',5'-cyclic adenosine monophosphate response element and other cis-acting elements in the human androgen receptor gene promoter. Mol Endocrinol. Jan. 1994;8(1):77-88.

Mowszowicz et al. Complete androgen insensitivity due to a single base substitution in exon 8 of the steroid-binding domain of the androgen receptor gene. *Endocrine* 1:203-209 (1993).

Narusaka et al. In vitro random mutagenesis of the D1 protein of the photosystem II reaction center confers phototolerance on the cyanobacterium Synechocystis sp. PCC 6803. J Biol Chem. Aug. 13, 1999;274(33):23270-5.

Newmark et al. Androgen receptor gene mutations in human prostate cancer. Proc Natl Acad Sci U S A. Jul. 15, 1992;89(14):6319-23.

Park et al. Effects of Conjugated Linoleic Acid on Body Composition in Mice *Lipids* 32(8):853-858 (1997).

Parker et al. Cancer statistics, 1997. CA Cancer J Clin. Jan.-Feb. 1997;47(1):5-27.

Pugh, Mechanisms of transcription complex assembly. Curr Opin Cell Biol. Jun. 1996;8(3):303-11.

Ruckle et al., Prostate-specific antigen and androgen deprivation therapy. World J Urol. 1993;11(4):227-32.

Sadler et al. Zyxin and cCRP: two interactive LIM domain proteins associated with the cytoskeleton. J Cell Biol. Dec. 1992;119(6):1573-87.

Sarkar et al. Analysis of retinoblastoma (RB) gene deletion in human prostatic carcinomas. Prostate. 1992;21(2);145-52.

Schmeichel & Beckerle, The LIM domain is a modular protein-binding interface. Cell. Oct. 21, 1994;79(2):211-9.

*Schmeichel and Beckerle* The LIM domain is a modular protein-binding interface. Cell. Oct. 21, 1994;79(2):211-9.

Shibanuma et al. Characterization of the TGF beta 1-inducible hic-5 gene that encodes a putative novel zinc finger protein and its possible involvement in cellular senescence. J Biol Chem. Oct. 28, 1994;269(43):26767-74.

Singh et al. A role for retinoblastoma protein in potentiating transcriptional activation by the glucocoticoid receptor. Nature. Apr. 6, 1995;374(6522):562-5.

Smith et al. CREB binding protein acts synergistically with steroid receptor coactivator-1 to enhance steroid receptor-dependent transcription. Proc Natl Acad Sci U S A. Aug. 20, 1996;93(17):8884-8.

Taplin et al. Mutation of the androgen-receptor gene in metastatic androgen-independent prostate cancer. N Engl J Med. May 25, 1995;332(21):1393-8.

Towbin et al. Electrophoretic transfer of proteins from polyacrylamide gels to nitrocellulose sheets: procedure and some applications. Proc Natl Acad Sci U S A. Sep. 1979;76(9):4350-4.

Truica et al. Beta-catenin affects androgen receptor transcriptional activity and ligand specificity. Cancer Res. Sep. 1, 2000;60(17):4709-13.

Ueki et al. Isolation and characterization of a novel human gene (HFB30) which encodes a protein with a RING finger motif. Biochim Biophys Acta. May 14, 1999;1445(2):232-6.

Van der Reijden, TRIADs: a new class of proteins with a novel cysteine-rich signature. Protein Sci. Jul. 1999;8(7):1557-61.

Veldscholte et al. A mutation in the ligand binding domain of the androgen receptor of human LNCaP cells affects steroid binding characteristics and response to anti-androgens. Biochem Biophys Res Commun. Dec. 14, 1990;173(2):534-40.

Wang, Ph.D. Thesis of University of Wisconsin-Madison (1997).

Weinberg, The retinoblastoma protein and cell cycle control. Cell. May 5, 1995;81(3):323-30.

Weintraub et al. Mechanism of active transcriptional repression by the retinoblastoma protein. Nature. Jun. 29, 1995;375(6534):812-5.

Yeh and Chang, Cloning and characterization of a specific coactivator, ARA70, for the androgen receptor in human prostate cells. Proc Natl Acad Sci U S A. May 28, 1996;93(11):5517-21.

Yeh et al. "Hydroxyflutamide may not always be a pure antiandrogen." Lancet. Mar. 22, 1997;349(9055):852-3.

Yeh et al. Differential induction of androgen receptor transactivation by different androgen receptor coactivators in human prostate cancer DU145 cells. Endocrine. Oct. 1999;11(2):195-202.

Yeh et al. From estrogen to androgen receptor: a new pathway for sex hormones in prostate. Proc Natl Acad Sci U S A. May 12, 1998;95(10):5527-32.

Yeh et al. From HER2/Neu signal cascade to androgen receptor and its coactivators: a novel pathway by induction of androgen target genes through MAP kinase in prostate cancer cells. Proc Natl Acad Sci U S A. May 11, 1999;96(10):5458-63.

Yeh et al. Increase of androgen-induced cell death and androgen receptor transactivation by BRCA1 in prostate cancer cells. Proc Natl Acad Sci U S A. Oct. 10, 2000;97(21):11256-61.

Yeh et al. Retinoblastoma, a tumor suppressor, is a coactivator for the androgen receptor in human prostate cancer DU145 cells. Biochem Biophys Res Commun. Jul. 20, 1998;248(2):361-7.

Zarkowska and Mittnacht, Differential phosphorylation of the retinoblastoma protein by G1/S cyclin-dependent kinases. J Biol Chem. May 9, 1997;272(19):12738-46.

ANDROGEN RECEPTOR COACTIVATORS

CROSS-REFERENCE TO RELATED APPLICATIONS

This application is a continuation of application Ser. No. 09/354,221, filed Jul. 15, 1999 (now U.S. Pat. No. 6,699,714), and which claims the benefit of U.S. Provisional Application No. 60/093,239, filed Jul. 17, 1998 and U.S. Provisional Application No. 60/100,243, filed Sep. 14, 1998.

STATEMENT REGARDING FEDERALLY SPONSORED RESEARCH OR DEVELOPMENT

Not applicable.

BACKGROUND OF THE INVENTION

Androgens constitute a class of hormones that control the development and proper function of mammalian male reproductive systems, including the prostate and epididymis. Androgens also affect the physiology of many non-reproductive systems, including muscle, skin, pituitary, lymphocytes, hair growth, and brain. Androgens exert their effect by altering the level of gene expression of specific genes in a process that is mediated by binding of androgen to an androgen receptor. The androgen receptor, which is a member of the steroid receptor super family, plays an important role in male sexual differentiation and in prostate cell proliferation. Binding of androgen by the androgen receptor allows the androgen receptor to interact with androgen responsive element (AREs), DNA sequences found on genes whose expression is regulated by androgen.

Androgen-mediated regulation of gene expression is a complicated process that may involve multiple co-activators (Adler et al., *Proc. National Acad. Sci. USA* 89:6319–6325, 1992). A fundamental question in the field of steroid hormone biology is how specific androgen-activated transcription can be achieved in vivo when several different receptors recognize the same DNA sequence. For example, the androgen receptor (AR), the glucocorticoid receptor (GR), and the progesterone receptor (PR) all recognize the same sequence but activate different transcription activities. Some have speculated that accessory factors may selectively interact with the androgen receptor to determine the specificity of gene activation by the androgen receptor.

Prostate cancer is the most common malignant neoplasm in aging males in the United States. Standard treatment includes the surgical or chemical castration of the patient in combination with the administration of anti-androgens such as 17 β estradiol (E2) or hydroxyflutamide (HF). However, most prostate cancers treated with androgen ablation and anti-androgens progress from an androgen-dependant to an androgen-independent state, causing a high incidence of relapse within 18 months (Crawford, *Br. J. Urology* 70: suppl. 1, 1992). The mechanisms by which prostate cancer cells become resistant to hormonal therapy remain unclear. One hypothesis that has been advanced is that over the course of treatment, a mutation in the AR occurs which alters the receptor's sensitivity to other steroid hormones or anti-androgens, such as E2 and HF, thereby causing the progression from androgen-dependent to androgen-independent prostate cancer. This hypothesis is supported by transient transfection assays in which it has been shown that anti-androgens may have an agonistic activity that stimulates mutant AR (mAR) mediated transcription.

Recently, A1B1 was identified as estrogen receptor coactivator that is expressed at higher levels in ovarian cancer cell lines and breast cancer cells than in noncancerous cells (Anzick, et al. *Science* 277:965–968, 1997). This result suggests that steroid hormone receptor cofactors may play an important role in the progression of certain diseases, such as hormone responsive tumors.

The identification, isolation, and characterization of genes that encode factors involved in the regulation of gene expression by androgen receptors will facilitate the development of screening assays to evaluate the potential efficacy of drugs in the treatment of prostate cancers.

BRIEF SUMMARY OF THE INVENTION

The present invention includes an isolated polynucleotide that encodes a co-activator for human androgen receptor, the polynucleotide comprising a sequence that encodes a polypeptide selected from the group consisting of an ARA54 polypeptide, an ARA55 polypeptide, an ARA24 polypeptide, and an Rb polypeptide.

Another aspect of the present invention is a genetic construct comprising a promoter functional in a prokaryotic or eukaryotic cell operably connected to a polynucleotide that encodes a polypeptide selected from the group consisting of an ARA54 polypeptide, an ARA55 polypeptide, an ARA24 polypeptide and an Rb polypeptide.

The present invention provides a method for screening candidate pharmaceutical molecules for the ability to promote or inhibit the interaction of ARs and AREs to modulate androgenic activity comprising the steps of:

(a) providing a genetic construct comprising a promoter functional in a eukaryotic cell operably connected to a polynucleotide comprising a sequence that encodes a polypeptide selected from the group consisting of an ARA54 polypeptide, an ARA55 polypeptide, an ARA24 polypeptide, and a retinoblastoma polypeptide;

(b) cotransforming a suitable eukaryotic cell with the construct of step a, and a construct comprising at least a portion of an expressible androgen receptor sequence;

(c) culturing the cells in the presence of a candidate pharmaceutical molecule; and (d) assaying the transcriptional activity induced by the androgen receptor.

It is an object of the present invention to a provide a genetic construct capable of expressing a factor involved in co-activation of the human androgen receptor.

It is an object of the present invention to provide a method for evaluating the ability of candidate pharmaceutical molecules to modulate the effect of androgen receptor coactivators on gene expression.

Other objects, features, and advantages of the present invention will become apparent upon reading the specification and claims.

DETAILED DESCRIPTION OF THE INVENTION

Transactivation of genes by the androgen receptor is a complicated system that involves many different coactivators. It is not currently known just how many factors are involved in androgen receptor-mediated regulation of gene expression. The identification and/or characterization of four androgen receptor coactivators is reported herein. Inclusion of one or more of these coactivators in an assay for androgenic and antiandrogenic activity is expected to increase the sensitivity of the assay. Information about these coactivators is valuable in the design of pharmaceutical agents intended to enhance or interfere with normal coactivator function. A preliminary assessment of the efficacy of a potential therapeutic agent can be made by evaluating the effect of the agent on the ability of the coactivator to enhance transactivation by the androgen receptor.

One aspect of the present invention is an isolated polynucleotide that encodes a co-activator for human androgen receptor, the polynucleotide comprising a sequence that encodes a polypeptide selected from the group consisting of an ARA54 polypeptide, an ARA55 polypeptide, an ARA24 polypeptide and an Rb polypeptide.

Another aspect of the present invention is a genetic construct comprising a promoter functional in a prokaryotic or eukaryotic cell operably connected to a polynucleotide that encodes a polypeptide selected from the group consisting of an ARA54 polypeptide, an ARA55 polypeptide, an ARA24 polypeptide and an Rb polypeptide.

The present invention includes a method for screening candidate pharmaceutical molecules for the ability to promote or inhibit the ARs and AREs to result in modulation of androgenic effect comprising the steps of:

(a) providing a genetic construct comprising a promoter functional in a eukaryotic cell operably connected to a polynucleotide comprising a sequence that encodes a polypeptide selected from the group consisting of an ARA54 polypeptide, an ARA55 polypeptide, an ARA24 polypeptide, and a retinoblastoma polypeptide;

(b) cotransforming a suitable eukaryotic cell with the construct of step a, and a construct comprising at least a portion of an expressible androgen receptor sequence;

(c) culturing the cells in the presence of a candidate pharmaceutical molecule; and (d) assaying the transcriptional activity induced by the androgen receptor gene.

The human androgen receptor is comprised of a ligand binding domain (LBD), a DNA binding domain (DBD), a hinge domain containing nuclear localization signals, and a transactivation domain in the hyper-variable N-terminus. Truncation or deletion of the LBD results in constitutive transactivation by the N-terminal domain.

In certain cases, progression of prostate cancer from androgen dependent- to androgen independent-stage may be caused by a mutation in the LBD that alters the ligand specificity of the mAR (Taplan et al., *New Engl. J. Med.* 332:1393–1398 (1995); Gaddipati et al., *Cancer Res.* 54:2861–2864 (1994)). We examined whether differential steroid specificity of wild type (wt) AR and mAR involves the use of different androgen receptor-associated (ARA) proteins or coactivators by these receptors.

As described in the examples, a yeast two-hybrid system with mARt887S as bait was used to screen the human prostate cDNA library. The sequences of two clones encoding a putative coactivators (designated ARA54 and ARA55) are shown in SEQ ID NO:1 and SEQ ID NO:3, respectively. The putative amino acid sequences of ARA54 and ARA55 are shown in SEQ ID NO:2 and SEQ ID NO:4, respectively. Also provided are the DNA and amino acid sequences of ARA24 (SEQ ID NO:5 and SEQ ID NO:6, respectively) and Rb (SEQ ID NO:7 and SEQ ID NO:8, respectively). These coactivators were further characterized as detailed below. It is expected that some minor variations from SEQ ID NOs: 1–8 associated with nucleotide additions, deletions, and mutations, whether naturally occurring or introduced in vitro, will not affect coactivation by the expression product or polypeptide.

Briefly, ARA54 is a 54 kDa protein that interacts with AR in an androgen-dependent manner. Coexpression of ARA54 and AR in a mammalian two-hybrid system demonstrated that reporter gene activity was enhanced in an androgen-dependent manner. ARA54 functions as a coactivator relatively specific for AR-mediated transcription. However, ARA54 may also function as a general coactivator of the transcriptional activity for other steroid receptors through their cognate ligands and response elements. ARA54 was found to enhance the transcriptional activity of AR and PR up to 6 fold and 3–5 fold, respectively. In contrast, ARA54 has only marginal effects (less than 2 fold) on glucocorticoid receptor (GR) and estrogen receptor (ER) in DU145 cells.

Coexpression of ARA54 with known AR coactivators SRC-1 or ARA70 revealed that each of these coactivators may contribute individually to achieve maximal AR-mediated transcriptional activity. Moreover, when ARA54 was expressed simultaneously with SRC-1 or ARA70, the increase in AR-mediated transactivation was additive but not synergistic relative to that observed in the presence of each coactivator alone.

The C-terminal domain of ARA54 (a.a. 361–471 of SEQ ID NO:1) serves as a dominant negative inhibitor of AR-mediated gene expression of target genes. Coexpression of exogenous full-length ARA54 can reduce this squelching effect in a dose-dependent manner.

ARA54 enhanced transactivation of wtAR in the presence of DHT ($10^{-10}$ to $10^{-8}$ M) by about 3–5 fold. However, transactivation of wtAR was enhanced only marginally with E2 ($10^{-9}$–$10^{-7}$ M) or HF ($10^{-7}$–$10^{-5}$ M) as the ligand. The ability of ARA54 to enhance transactivation by two mutant receptors (mARt877a and mARe708k) that exhibit differential sensitivities to E2 and HF (Yeh et al., *Proc. Natl. Acad. Sci. USA*, in press (1998)) was also examined. The mutant mARt877a, which is found in many prostate tumors (23), was activated by E2 ($10^{-9}$–$10^{-7}$ M) and HF ($10^{-7}$–$10^{-5}$ M), and ARA54 could further enhance E2- or HF-mediated AR transactivation. In contrast, the mutant mARe708k, first identified in a yeast genetic screening (Wang, C., Ph.D. *Thesis of University of Wisconsin-Madison* (1997)), exhibited ligand specificity and response to ARE54 comparable to that of wtAR.

It is expected that any polypeptide having substantial homology to ARA54 that still actuates the same biological effect can function as "an ARA54 polypeptide." With the sequence information disclosed herein, one skilled in the art can obtain any ARA54 polypeptide using standard molecular biological techniques. An ARA54 polypeptide is a polypeptide that is capable of enhancing transactivation of AR in an androgen-dependent manner, enhancing E2 or HF transactivation by the mutant receptor mARt877a, and reducing inhibition of AR-mediated gene expression caused by overexpression of the C-terminal domain of ARA54 (a.a. 361–471 of SEQ ID NO:1). The sequence information presented in this application can be used to identify, clone or sequence allelic variations in the ARA54 genes as well as the counterpart genes from other mammalian species it is also contemplate that truncations of the native coding region can be made to express smaller polypeptides that will retain the same biological activity.

The polynucleotide sequence of ARA55 (SEQ ID NO:3) exhibits high homology to the C-terminus of mouse hic5 (hydrogen peroxide inducible clone) (Pugh, B., *Curr. Opin. Cell Biol.* 8:303–311 (1996)), and like hic5, ARA55 expression is induced by TGFb. Cotransfection assays of transcriptional activation, which are described in detail below, revealed that ARA55 is able to bind to both wtAR and mART887S in a ligand-dependent manner to enhance AR transcriptional activities. ARA55 enhanced transcriptional activation by wtAR in the presence of $10^{-9}$M DHT or T, but not $10^{-9}$M E2 or HF. In contrast, ARA55 can enhance transcriptional activation by mART887S in the presence of DHT, testosterone (T), E2, or HF. ARA55 did not enhance transcriptional activation of mARe708k in the presence of E2, but can enhance transcription in the presence of DHT or T.

The C-terminal domain of ARA55 (amino acids 251–444 of SEQ ID NO:3) is sufficient for binding to ARs, but does not enhance transcriptional activation by ARs.

The invention is not limited to the particular ARA55 polypeptide disclosed in SEQ ID NO:4. It is expected that any ARA55 polypeptide could be used in the practice of the present invention. By "an ARA55 polypeptide" it meant a polypeptide that is capable of enhancing transactivation of wtAR, the mutant receptor mARt877a, in the presence of DHT, E2, or HF or intact receptor mARe708k in the presence of DHT or T. Such polypeptides include allelic variants and the corresponding genes from other mammalian species as well as truncations.

The AR N-terminal domain comprises a polymorphic poly-glutamine (Q) stretch and a polymorphic poly-glycine (G) stretch that account for variability in the length of human AR cDNA observed. The length of the poly-Q region (normally 11–33 residues in length) is inversely correlated with the risk of prostate cancer, and directly correlated with the SBMA, or Kennedy's disease (La Spada et al., *Nature (London)* 352:77–79 (1991)). The incidence of higher grade, distant metastatic, and fatal prostate cancer is higher in men having shorter AR poly-Q stretches.

As described in the examples, experiments undertaken to identify potential coactivators that interact with the AR poly-Q region led to the isolation of a clone encoding a coactivator, designated ARA24, that interacts with the poly-Q region. The sequences of the ARA24 clone and its putative translation product is shown in SEQ ID NO:5 and SEQ ID NO:6.

The ARA24 clone has an ORF that is identical to the published ORF for human Ran, an abundant, ras-like small GTPase (Beddow et al. *Proc. Natl. Acad. Sci. USA* 92:3328–3332, 1995). Overexpression of ARA24 in the presence of DHT does enhance transcriptional activation by AR over that observed in cells transfected with AR alone. Moreover, expression of antisense ARA24 (ARA24as) does reduce DHT-induced transcriptional activation.

An ARA24 polypeptide is one that interacts with the poly-Q region of an AR. An ARA24 polypeptide is further characterized by its ability to increase transactivation when overexpressed in eukaryotic cells having some endogenous ARA24, but expression of an ARA24 antisense RNA reduces AR receptor transactivation.

Androgen receptor mutations do not account for all cases of androgen-independent tumors, because some androgen-independent tumors retain wild-type AR. A significant percentage of androgen-insensitive tumors have been correlated with reduced expression of retinoblastoma protein (Rb) (Bookstein, et al., *Science* 247:712–715, (1990)), expression a truncated Rb protein (Bookstein, et al. *Proc. Natl. Acad. Sci. USA* 87:7762–7766 (1990)), or a missing Rb allele (Brooks, et al. *Prostate* 26:35–39, (1995)). The prostate cancer cell line DU145 has an abnormal short mRNA transcript of Rb exon 21 (Sarkar, et al. *Prostate* 21:145–152 (1992)) and transfecton of the wild-type Rb gene into DU145 cells was shown to repress the malignant phenotype (Bookstein, et al. *Proc. Natl. Acad. Sci. USA* 87:7762–7766 (1990)).

Rb functions in the control of cell proliferation and differentiation (Weinberg, R. A., *Cell* 81:323–330 (1995); Kranenburg et al., *FEBS Lett.* 367:103–106 (1995)). In resting cells, hypophophorylated Rb prevents inappropriate entry of cells into the cell division cycle. Phosphorylation of Rb by cyclin-dependent kinases relieves Rb-mediated growth suppression, and allows for cell proliferation (Dowdy et al., *Cell* 73:499–511 (1993); Chen et al., *Cell* 58:1193–1198 (1989)). Conversely, dephosphorylation of Rb during G1 progression induces growth arrest or cell differentiation (Chen et al. (1989); Mihara et al., *Science* 246:1300–1303 (1989)). In dividing cells, Rb is dephosphorylated during mitotic exit and G1 entry (Ludlow et al., *Mol. Cell. Biol.* 13:367–372 (1993)). This dephosphorylation activates Rb for the ensuing G1 phase of the cell cycle, during which Rb exerts it growth suppressive effects.

We investigated the role of Rb in AR transactivation as detailed in the examples. We found that Rb can induce transcriptional activity of wtAR or mARs877t in the presence of DHT, E2, or HF, and mARe708k in the presence of DHT. We also discovered that Rb and ARA70 transcriptional activity act synergistically to enhance transcriptional activity of ARs. The sequence of the cloned Rb gene and the deduced amino acid sequence of the ORF are shown in SEQ ID NO:7 and SEQ ID NO:8, respectively. An Rb polypeptide is a polypeptide that is substantially homologous to SEQ ID NO:8, that interacts with the N-terminal domain of AR, and which acts synergistically with ARA70 in enhancing transactivation by AR.

In the examples, various eukaryotic cell types, including yeast, prostate cells having mutant AR and cells lacking AR, were used to evaluate the ability of the putative androgen coactivators to enhance transactivation by AR. It is expected that in the method of the present invention, any eukaryotic cell could be employed in an assay for AR activity. This feature allows the investigator flexibility in designing assays.

As described below, cells were transfected using a calcium phosphate technique. It is expected that the method of the present invention could be practiced using any transfection means including, for example, electroporation or particle bombardment.

Changes in the level of transactivation by AR can be assessed by any means, including measuring changes in the level of mRNA for a gene under the control of AR, or by quantitating the amount of a particular protein expressed using an antibody specific for a protein, the expression of which is under the control of AR. Most conveniently, transactivation by AR can be assessed by means of a reporter gene.

As used herein, a reporter gene is a gene under the control of an androgen receptor, the gene encoding a protein susceptible to quantitation by a colormetric or fluorescent assay. In the examples below, a chloramphenicol acetyltransferase or a luciferase gene were used as reporter genes. The gene may either be resident in a chromosome of the host cell, or may be introduced into the host cell by cotransfection with the coactivator gene.

The following nonlimiting examples are intended to be purely illustrative.

EXAMPLES

Plasmid Construction

A human prostate library in pACT2 yeast expression vector (a gift from Dr. S. Elledge) consists of the GAL4 activation domain (GAL4AD, a.a. 768–881) fused with human prostate cDNA.

pSG5 wtAR was constructed as described previously (Yeh and Chang, *Proc. Natl. Acad. Sci USA* 93:5517–5521, 1996).

pGAL0-AR (wild-type) was obtained from D. Chen (University of Massachusetts). pGAL0 contains the GAL4 DNA binding domain (DBD).

For construction of pAS2-wtAR or -mAR, the C-terminal fragments (aa 595–918) from wtAR, mARt877s (Dr. S. P. Balk, Beth Israel Hospital, Boston, Mass.), or mARe708k (H. Shim, Hyogo Medical College, Japan) were inserted in pAS2 yeast expression vector (Clontech). Another AR mutant (mARv888m), derived from androgen insensitive syndrome patient, was constructed as previously described (Mowszowicz, et al. *Endocrine* 1:203–209, 1993).

pGAL4-VP16 was used to construct a fusion of ARA70. pGAL4-VP16 contains the GAL4 DBD linked to the acidic activation domain of VP16.

pCMX-Gal-N-RB and pCMX-VP16-AR were constructed by inserting fragments Rb (aa 370–928) and AR (aa 590–918) into pCMX-gal-N and pCMX-VP16, respectively. The sequence of construction junction was verified by sequencing.

pYX-ARA24/Ran was constructed by placing the ARA24 gene under the control of the gal-1 promoter of yeast expression plasmid pYX243 (Ingenus). A cDNA fragment encoding the AR poly-Q stretch and its flanking regions (AR a.a. 11–208) was ligated to a PAS2 yeast expression plasmid for use as bait in the two hybrid assay. AR cDNAs of different poly-Q lengths that span the same AR poly-Q region as our bait plasmid were constructed in pAS2 in the same way, for yeast two-hybrid liquid culture β-gal assay. These AR bait plasmids with poly-Q lengths of 1, 25, 49 were all transformed into yeast Y190 and found to not be autonomously active. pCMV-antisense ARA24/Ran (ARA24 as) expression plasmid was constructed by inserting a 334-bp Bgl II fragment of ARA24/Ran, which spans 5'-untranslated region and the translation start codon of ARA24/Ran (nucleotides 1–334 of SEQ ID NO:5), into pCMV vector in the antisense orientation. The MMTV-CAT and MMTV-Luc reporter genes were used for AR transactivation assay. pSG5-AR and pSV-βgal are under the regulation of SV40 promoter and β-globulin gene intron-1 enhancer. p6R-ARQ1, p6R-ARQ25, p6R-ARQ49 were kindly provided by Dr. Roger L. Meisfield (Chamberlain, et al. *Nucleic Acids Res.* 22:3181–3186, 1994)

pSG5-GAL4DBD-ARA24 was generated by inserting the coding sequence of Gal4DBD-ARA24 hybrid protein into pSG5 vector. pVP16-ARN-Q1, pVP16-ARN-Q25, pVP16-ARN-Q25, pVP16-ARN-Q35, pVP16-ARN-Q49 were generated by inserting each poly-Q AR N-terminal domain (a.a. 34–555) into pVP16 vector (Clontech) to be expressed as a VP16AD hybrid protein. GAL0AR plasmid, which contains GAL4DBD fused to E region of human AR, was a gift from Dr. D. Chen. The pSG5-CAT reporter plasmid (Clontech) contains five GAL4 binding sites upstream of the E1b TATA box, linked to the CAT gene.

pSG5-AR and pSG5-ARA70 were constructed as previously described (Yeh and Chang, *Proc. Natl. Acad. Sci USA* 93:5517–5521, 1996). Two mutants of the AR gene (mAR877 derived from prostate cancer, codon 877 mutation Thr to Ala; and mAR708 derived from partial androgen insensitive syndrome (PIAS), codon 708 mutation Glu to Lys), were provided by S. Balk (Beth Israel Hospital, Boston) and H. Shima (Hyogo Medical College, Japan), respectively.

Clones used in the two-hybrid system to evaluate the role of Rb in AR transactivation were made by ligating an Rb fragment (aa 371–928) to the DBD of GAL4. Similarly, near full-length (aa 36–918) AR (nAR) and AR-LBD (aa 590–918) fragments ligated to transcriptional activator VP16.

Screening of Prostate cDNA Library by a Yeast Two-hybrid System for ARAs Associated with the Ligand Binding Domain To identify ARA coactivators interact with the LBD, a pACT2-prostate cDNA library was cotransformed into Y190 yeast cells with a plasmid of pAS2 mAR (mART877S) which contains GAL4DBD (aa 1–147) fused with the C-terminal domain of this mAR. Transformants were selected for growth on SD plates with 3-aminotriazole (25 mM) and DHT (100 nM) lacking histidine, leucine and tryptophan (–3SD plates). Colonies were also filter-assayed for β-galactosidase activity. Plasmid DNA from positive cDNA clones were found to interact with mtARt877s but not GAL4TR4 was isolated from yeast, amplified in *E. coli*, and the inserts confirmed by DNA sequencing.

To identify clones that interact with the poly-Q region of the N-terminal domain, the AR poly-Q stretch (aa 11–208) was inserted into the pAS2 yeast expression plasmid and cotransformed into Y190 yeast cells with a human brain cDNA library fused to the Gal4 activation domain. Transformants were selected for growth on SD plates lacking histidine, leucine and tryptophan and supplemented with 3-aminotriazole (40 mM).

Amplification and Characterization of ARA Clones

Full length DNA sequences comprising two coactivators, designated ARA54 (SEQ ID NO:1) and ARA55 (SEQ ID NO:3), that were found to interact with mARt877s were isolated by 5' RACE PCR using Marathon cDNA Amplification Kit (Clontech) according to the manufacturer's protocol.

The missing 5' coding region of the ARA54 gene was isolated from H1299 cells using the gene-specific antisense primer shown in SEQ ID NO:9 and following PCR reaction conditions: 94° C. for 1 min, 5 cycles of 94° C. for 5 sec→72° C. for 3 min, 5 cycles of 94° C. for 5 sec→70° C. for 3 min, then 25 cycles of 94° C. for 5 sec→68° C. for 3 min. The PCR product was subcloned into pT7-Blue vector (Novagen) and sequenced.

ARA55 was amplified by PCR from the HeLa cell line using an ARA55-specific antisense primer (SEQ ID NO:10) and the PCR reaction conditions described for isolation of ARA54.

Using the 5' RACE-PCR method, we were able to isolate a 1721 bp DNA fragment (SEQ ID NO:1) from the H1299 cell line with an open reading frame that encodes a novel protein 474 amino acids in length (SEQ ID NO:2). The in-vitro translation product is a polypeptide with an apparent molecular mass of 54±2 kDA, consistent with the calculated molecular weight (53.8 kDa). The middle portion of ARA54 (a.a. 220–265 of SEQ ID NO:2) contains a cysteine-rich region that may form a zinc finger motif called the RING finger, defined as $CX_2CX_{9-27}CXHX_2CX_2CX_{6-17}CX_2C$ (SEQ ID NO: 11), a domain conserved among several human transcriptional factor or proto-oncogeny proteins, including BRCA1, RING1, PML and MEL-18 (Miki et al., *Science* 266:66–71 (1994); Borden et al., *EMBO J.* 14:1532–1541 (1995); Lovering et al., *Proc. Natl. Acad. Sci. USA* 90:2112–2116 (1993); Blake et al., *Oncogene* 6: 653–657 (1991); Ishida et al, *Gene* 129:249–255 (1993)). In addition, ARA54 also contains a second cysteine-rich motif which has a B box like structure located at 43 amino acids downstream from the RING finger motif. However, ARA54 differs from members of the RING finger-B-box family in that it lacks a predicted coiled-coil domain immediately C-terminal to the B box domain, which is highly conserved in the RING finger-B-box family. Therefore, ARA54 may represent a new subgroup of this family.

The full-length human ARA55 has an open reading frame that encodes a 444 aa polypeptide (SEQ ID NO:4) with a predicted molecular weight of 55 kD that ARA55 shares 91% homology with mouse hic5. Human ARA55 has four LIM motifs in the C-terminal region. An LIM motif is a cysteine-rich zinc-binding motif with consensus sequence: $CX_2CX_{16-23}HX_2CX_2CX_2CX_{16-21}CX_2$ (C, H, D) (SEQ ID NO:12) (Sadler, et al., *J. Cell Biol.* 119:1573–1587 (1992)). Although the function of the LIM motif has not been fully defined, some data suggest that it may play a role in protein-protein interaction (Schmeichel & Beckerle, *Cell* 79:211–219, 1994). Among all identified SR associated proteins, only ARA55 and thyroid hormone interacting protein 6 (Trip 6) (Lee, et al. *Mol. Endocrinol.* 9:243–254 (1995)) have LIM motifs.

A clone that showed strong interaction with the poly-Q bait was identified and subsequently subjected to sequence analysis. This clone contains 1566 bp insert (SEQ ID NO:5) with an open reading frame encoding a 216 aa polypeptide (SEQ ID NO:6) with a calculated molecular weight of 24 kDa. GenBank sequence comparison showed that this clone has the same open reading frame sequence as Ran/TC4, an abundant ras-like small GTPase involved in nucleocytoplasmic transport that is found in a wide variety of cell types (Beddow et al., *Proc. Natl. Acad. Sci. U.S.A.* 92:3328–3332, 1995). Accordingly, the factor was designated ARA24/Ran. The cDNA sequence of the ARA24 clone (SEQ ID NO:5) (GenBank accession number AF052578) is longer than that of the published ORF for human Ran, in that it includes 24 and 891 bp of 5'- and 3'-untranslated regions, respectively.

Northern Blotting

The total RNA (25 µg) was fractionated on a 1% formaldehyde-MOPS agarose gel, transferred onto a Hybond-N nylon membrane (Amersham) and prehybridized. A probe corresponding to the 900 bp C-terminus of ARA55 or an ARA54-specific sequence was $^{32}$P-labeled in vitro using Random Primed DNA Labeling Kit (Boehringer-Mannheim) according to the manufacture's protocol and hybridized overnight. After washing, the blot was exposed and quantified by Molecular Dynamics PhosphorImager. β-actin was used to monitor the amount of total RNA in each lane.

Northern blot analysis indicated the presence of a 2 kb ARA55 transcript in Hela and prostate PC3 cells. The transcript was not detected in other tested cell lines, including HepG2, H1299, MCF7, CHO, PC12, P19, and DU145 cells. The ARA54 transcript was found in H1299 cells, as well as in prostate cancer cell lines PC3 and LNCaP.

Co-immunoprecipitation of AR and ARAs

Lysates from in-vitro translated full-length of AR and ARA54 were incubated with or without $10^{-8}$ M DHT in the modified RIPA buffer (50 mM Tris-HCL pH 7.4, 150 mM NaCl, 5 mM EDTA, 0.1% NP40, 1 mM PMSF, aprotinin, leupeptin, pepstatin, 0.25% Na-deoxycholate, 0.25% gelatin) and rocked at 4° C. for 2 hr. The mixture was incubated with rabbit anti-His.tag polyclonal antibodies for another 2 hr and protein A/G PLUS—Agarose (Santa Cruz) were added and incubated at 4° C. for additional 2 hr. The conjugated beads were washed 4 times with RIPA buffer, boiled in SDS sample buffer and analyzed by 8% SDS/PAGE and visualized by STORM 840 (Molecular Dynamics).

ARA54 and AR were found in a complex when immunoprecipitated in the presence of $10^{-8}$ M DHT, but not in the absence of DHT. This result suggests that ARA54 interacts with AR in an androgen-dependent manner.

Interaction between recombinant full length human AR and ARA24/Ran proteins further examined by co-immunoprecipitation, followed by SDS-PAGE and western blotting. Results of the co-immunoprecipitation assay indicate that ARA24/Ran interacts directly with AR. The phosphorylation state of bound guanine nucleotide to the small GTPases does not affect this interaction.

AR Pull-down Assay Using GST-Rb

Full-length Rb fused to glutathione-S-transferase (ST-Rb$_{1-928}$) was expressed and purified from *E. coli.* strain Bl21pLys as described recently (Zarkowska & Mittnacht, *J. Biol. Chem.* 272:12738–12746, 1997). Approximately 2 µg of His-tag column purified baculovirus AR was mixed with GST-loaded glutathione-Sepharose beads in 1 ml of NET-N (20 mM Tris-HCL (pH 8.0, 100 mM NaCl, 1 mM EDTA, 0.5% (v/v) Noniodet P-40) and incubated with gentle rocking for 3 hr at 4° C.

Following low-speed centrifugation to pellet the beads, the clarified supernatant was mixed with GST-Rb-loaded glutathione-Sepharose beads in the presence or absence of 10 mM DHT and incubated for an additional 3 hr with gentle rocking at 4° C. The pelleted beads were washed 5 times with NET-N, mixed with SDS-sample buffer, boiled, and the proteins separated by electrophoresis on a 7.5% polyacrylamide gel. A Western blot of the gel was incubated with anti-AR polyclonal antibody NH27 and developed with alkaline phosphatase-conjugated secondary antibodies.

AR was coprecipitated with GST-Rb, but not GST alone, indicating that AR and Rb are associated in a complex together.

Transfection Studies

Human prostate cancer DU145 or PC3 cells, or human lung carcinoma cells NCI H1299 were grown in Dulbecco's minimal essential medium (DMEM) containing penicillin (25 U/ml), streptomycin (25 µg/ml), and 5% fetal calf serum (FCS). One hour before transfection, the medium was changed to DMEM with 5% charcoal-stripped FCS. Phenol red-free and serum-free media were used on the experiments employing E2 or TGFβ, respectively. A β-galactosidase expression plasmid, pCMV-β-gal, was used as an internal control for transfection efficiency.

Cells were transfected using the calcium phosphate technique (Yeh, et al. *Molec. Endocrinol.* 8:77–88, 1994). The medium was changed 24 hr posttransfection and the cells treated with either steroid hormones or hydroxyflutamide, and cultured for an additional 24 hr. Cells were harvested and assayed for CAT activity after the cell lysates were normalized by using β-galactosidase as an internal control. Chloramphenicol acetyltransferase (CAT) activity was visualized by PhosphorImager (Molecular Dynamics) and quantitated by ImageQuant software (Molecular Dynamics).

Mammalian Two-Hybrid Assay

The mammalian two-hybrid system employed was essentially the protocol of Clontech (California), with the following modifications. In order to obtain better expression, the GAL4DBD (a.a. 1–147) was fused to pSG5 under the control of an SV40 promoter, and named pGAL0. The hinge and LBD of wtAR were then inserted into pGAL0. Similarly, the VP16 activation domain was fused to pCMX under the control of a CMV promoter, and designated pCMX-VP16 (provided by Dr. R. M. Evan).

The DHT-dependent interaction between AR and ARA54 was confirmed in prostate DU145 cells using two-hybrid system with CAT reporter gene assay. Transient transfection of either ARA54 or wtAR alone showed negligible transcriptional activity. However, coexpression of AR with ARA54 in the presence of $10^{-8}$ M DHT significantly induced CAT activity.

ARA54 functions as a coactivator relatively specific for AR-mediated transcription. ARA54 induces the transcriptional activity of AR and PR by up to 6 fold and 3–5 fold, respectively. In contrast, ARA54 showed only marginal effects (less than 2 fold) on GR and ER in DU145 cells. These data suggest that ARA54 is less specific to AR as relative to ARA70, which shows higher specificity to AR. However, we can not rule out the possibility that ARA54 might be more general to other steroid receptors in other cell types under different conditions.

Coexpression of ARA54 with SRC-1 or ARA70 was found to enhance AR transcriptional activity additively rather than synergistically. These results indicate that these cofactors may contribute individually to the proper or maximal AR-mediated transcriptional activity.

Since the C-terminal region of ARA54 (a.a. 361–471 of SEQ ID NO:2) isolated from prostate cDNA library has shown to be sufficient to interact with AR in yeast two-hybrid assays, we further investigated whether it could squelch the effect of ARA54 on AR-activated transcription in H1299 cells, which contain endogenous ARA54. The C-terminal region of ARA54 inhibits AR-mediated transcription by up to 70%; coexpression of exogenous full-length ARA54 reverses this squelching effect in a dose-dependent manner. These results demonstrate that the C-terminal domain of ARA54 can serve as a dominant negative inhibitor, and that ARA54 is required for the proper or maximal AR transactivation in human H1299 cells.

Examination of the effect of ARA54 on the transcriptional activities of wtAR and mtARs in the presence of DHT, E2 and HF revealed differential ligand specificity. Translational activation of wtAR occurred in the presence of DHT ($10^{-10}$ to $10^{-8}$ M); coexpression of ARA54 enhanced transactivation by another 3–5 fold. However, wtAR responded only marginally to E2 ($10^{-9}$–$10^{-7}$ M) or HF ($10^{-7}$–$10^{-5}$ M) in the presence or absence of ARA54. As expected, the positive control, ARA70, is able to enhance the AR transcriptional activity in the presence of $10^{-9}$–$10^{-7}$ M E2 and $10^{-7}$–$10^{-5}$ HF, that matches well with previous reports (Yeh, PNAS, Miyamoto, PNAS).

The AR mutants Art877a, which is found in many prostate tumors (23), and Are708k, found in a yeast genetic screening (24) and a patient with partial androgen insensitivity, exhibited differential specificity for lignands. In the absence of ARA54, Art877a responded to E2 ($10^{-9}$–$10^{-7}$ M) and HF ($10^{-7}$–$10^{-5}$ M), and ARA54 could further enhance E2- or HF-mediated AR transactivation. These results suggested that mtARs might also require cofactors for the proper or maximal DHT-, E2-, or HF-mediated AR transcriptional activity. The DHT response of mARe708k was only a slightly less sensitive than that of wtAR or mARt877s, whereas E2 and HF exhibited no agonistic activity toward ARe708k. Together, these results imply that the change of residue 708 on AR might be critical for the interaction of the antiandrogen-ARe708k-ARA54 complex, and that both AR structure and coactivators may play a role in determining ligand specificity.

CAT activity in DU145 cells cotransfected with a plasmid encoding the hormone binding domain of wtAR fused to the GAL4 DBD (GAL0AR) and a plasmid encoding full-length ARA55 fused to the activation domain of VP16 (VP16-ARA55) was significantly induced by the cotransfection of VP16-ARA55 and GAL0AR in the presence of 10 nM DHT, but not induced by E2 or HF. Combination of GAL0 empty vector and VP16-ARA55 did not show any CAT activity. Combination of GAL0AR and VP16 vector showed negligible CAT activity. These results indicate that ARA55 interacts with AR in an androgen-dependent manner.

Transient transfection assays were conducted to investigate the role of ARA55 in the transactivation activity of AR. DU145 cells were cotransfected with MMTV-CAT reporter, increasing amounts of ARA55 and wtAR under eukaryotic promoter control. Ligand-free AR has minimal MMTV-CAT reporter activity in the presence or absence of ARA55. ARA55 alone also has only minimal reporter activity Addition of 10 nM DHT resulted in 4.3 fold increase of AR transcriptional activity and ARA55 further increased this induction by 5.3 fold (from 4.3 fold to 22.8 fold) in a dose-dependent manner. The induced activity reached a plateau at the ratio of AR:ARA55 to 1:4.5. Similar results were obtained using PC3 cells with DU145 cells, or using a CAT reporter gene under the control of a 2.8 kb promoter region of a PSA gene. The C-terminus of ARA55 (ARA55$_{251-444}$) (a.a. 251–444 of SEQ ID NO:4) did not enhance CAT activity. Cotransfection of PC3 cells, which contain endogenous ARA55, with ARA55$_{251-444}$, AR and MMTV-CAT reporter in the presence of 10 nM DHT demonstrated dramatically reduced AR transcriptional activity relative to cells transfected with AR and MMTV-CAT alone. These results demonstrate that ARA55 is required for the proper or maximal AR transcriptional activity in PC3 cells, and that the C-terminus of ARA55 can serve as a dominant negative inhibitor.

The effect of ARA55 on mARt877s and mARe708k in the presence of DHT and its antagonists, E2, and HF. The mARt877s receptor is found in LNCaP cells and/or advanced prostate cancers and has a point mutation at codon 877 (Thr to Ser) (Gaddipati et al., *Cancer Res.* 54:2861–2864 (1994); Veldscholte et al., *Biochem. Biophys. Commun.* 173:534–540 (1990)). The mARe708k receptor, has a point mutation at codon 708 (Glu to Lys), was isolated by a yeast genetic screening and exhibits reduced sensitivity to HF and E2 relative to wtAR (Wang, C., *PhD thesis of University of Wisconsin-Madison* (1997)). The transcriptional activities of wtAR, mARt877s, and mARe708k are induced by DHT ($10^{-11}$ to $10^{-8}$ M). ARA55 enhanced the transactivation of all three receptors by 4–8 fold. In the presence of E2 or HF, wtAR responded marginally only at higher concentrations ($10^{-7}$ M for E2 and $10^{-5}$ M for HF). Cotransfection of wtAR with ARA55 at a 1:4.5 ratio, however, increases AR transcriptional activity at $10^{-8}$–$10^{-7}$ M for E2 or $10^{-6}$ to $10^{-5}$ M for HF. Compared to wtAR, the LNCaP mAR responded much better to E2 and HF and ARA55 significantly enhanced its transcriptional activity. ARA55 may be needed for the proper or maximal DHT-, E2-, or HF-mediated AR transcriptional activity.

The effect of ARA55 on transcriptional activation by GR, PR, and ER was tested in DU145 cells. ARA55 is relatively specific to AR, although it may also enhance GR and PR to a lesser degree, and has only a marginal effect on ER. ARA70 shows much higher specificity to AR than ARA55, relative to the other tested steroid receptors. Although ARA55 enhances AR-mediated transcription to a greater degree than GR-, PR-, or ER-mediated transcription, it appears to be less specific than ARA70.

Because the amino acid sequence of ARA55 has very high homology to mouse hic5, and early studies hic5 suggested this mouse gene expression can be induced by the negative TGFβ (Shibanuma et al., *J. Biol. Chem.* 269:26767–26774 (1994)), we were interested to see whether ARA55 could serve as a bridge between TGFβ and AR steroid hormone system. Northern blot—analysis indicated that TGFβ treatment (5 ng/ml) could induce ARA55 mRNA by 2-fold in PC3 cells. In the same cells, TGFβ treatment increased AR transcriptional activity by 70%. This induction is weak relative to the affect achieved upon transfection of PC3 cells with exogenous ARA55 (70% vs. 4 fold). This may be related to the differences in the ratios of AR and ARA55. The best ratio of AR:ARA55 for maximal AR transcriptional activity is 1:4.5. Whether other mechanisms may also be involve in this TGFβ-induced AR transcriptional activity will be an interesting question to investigate. The unexpected discovery that TGFβ may increase AR transcriptional activity via induction of ARA55 in prostate may represent the first evidence to link a negative regulatory protein function in a positive manner, by inducing the transcriptional activity of AR, the major promoter for the prostate tumor growth.

The ability of ARA55 to induce transcriptional activity of both wtAR and mARt877s in the presence of DHT, E2, and HF suggests an important role for ARA55 in the progression of prostate cancer and the development of resistance to hormonal therapy. Evaluation of molecules that interfere with the function of ARA55 may aid in the identification of potential chemotherapeutic pharmaceuticals.

Human small lung carcinoma H1299 cell line, which has no endogenous AR protein, were transfected with AR and ARA24/Ran. Because ARA24/Ran is one of the most abundant and ubiquitously expressed proteins in various cells, both sense and antisense ARA24/Ran mammalian expression plasmids were tested. Overexpression of sense ARA24/Ran did not significantly enhance the AR transactivation, a result that is not surprising, in view of the abundance of endogenous ARA24/RAN. However, expression of anti-sense ARA24/Ran (ARA24as) markedly decreased DHT-induced CAT activity in a dose dependent manner. Furthermore, increasing the DHT concentration from 0.1 nM to 10 nM DHT resulted in strong induction of AR transactivation and decreased the inhibitory effect of ARA24 as effect, indicating that increased DHT concentration can antagonize the negative effect of ARA24 as.

The affinity between ARA24/Ran and AR is inversely related to the length of AR poly-Q stretch. AR transactivation decreases with increasing AR poly-Q length. Reciprocal two-hybrid assays with exchanged fusion partners, Gal4DBD-ARA24/Ran and VP16AD-ARNs (a.a. 34–555 with poly-Q lengths of 1, 25, 35, 49 residues) were conducted using mammalian CHO cells. These results consistently show that the affinity between ARA24/Ran and AR poly-Q region is inversely correlated with AR poly-Q length in both yeast and mammalian CHO cells.

The regulation of AR transactivation by ARA24/Ran correlates with their affinity. These results suggest that ARA24/Ran could achieve differential transactivation of AR, with ARs having different poly-Q length could existing in a single cell or cell system. ARA24 as was again used in the ARE-Luc transfection assays to address the role of AR poly-Q length in the regulation of AR by ARA24/Ran. ARs of poly-Q lengths 1, 25, and 49 residues, and increasing amounts (1, 2, and 4 μg) of ARA24 as expression vectors were co-transfected with equal amounts of reporter plasmid (pMMTV-Luc) in CHO cells. Although the basal reporter activity is slightly affected by increasing amounts of anti-sense ARA24/Ran, ARA24 as showed a more significant decrease of AR transactivation. As AR poly-Q length increased, the ARA24 as effect on AR transactivation decreased. These results suggest that the affinity of ARA24/Ran for AR and the effect of decreasing ARA24/Ran on AR transactivation faded over the expansion of AR poly-Q length.

Coexpression of Rb and AR expression plasmids in DU145 cells using the mammalian two-hybrid system resulted in a 3 fold increase in CAT activity by cotransfection of near full length AR (nAR, amino acids 36–918) and Rb. Cells cotransfected with nAR and PR-LBD or Rb and ARA70 did not show increased CAT activity. Surprisingly, addition of 10 nM DHT made very little difference in the interaction between Rb and nAR. The inability of Rb to interact with AR-LBD suggest that interaction site of AR is located in N-terminal domain (aa 36 to 590). Together, our data suggest the interaction between Rb and AR is unique in the following ways: first, the interaction is androgen-independent and binding is specific but relatively weak as compared to other AR associated protein, such as ARA70 (3 fold vs. 12 fold induced CAT activity in mammalian two-hybrid assay, data not shown). Second, unlike most identified steroid receptor associated proteins that bind to C-terminal domain of steroid receptor, Rb binds to N-terminal domain of AR. Third, no interaction occurred between Rb and ARA70, two AR associated proteins in DU145 cells.

DU145 cells containing mutated Rb (Singh et al., *Nature* 374: 562–565 (1995)) were cultured with charcoal-stripped FCS in the presence or absence of 1 nM DHT. No AR transcriptional activity was observed in DU145 cells transiently transfected with wild type AR and Rb at the ratio of 1:3 in the absence of DHT. When However, AR transcriptional activity could be induced 5-fold when wild type AR was expressed in the presence of 1 nM DHT. Cotransfection of Rb with AR can further enhance the AR transcriptional activity from 5-fold to 21-fold in the presence of 1 nM DHT. As a control, cotransfection of ARA70, the first identified AR coactivator, can further enhance in DU145 cells transcriptional activity from 5-fold to 36-fold. In DU145 cells transfected with Rb, ARA70, and AR, the induction of AR transcriptional activity was synergistically increased from 5-fold to 64-fold. Upon transfection of wild type AR without Rb or ARA70, only marginal induction (less than 2-fold) was detected in the presence of 10 nM E2 or 1 μM HF. In contrast, cotransfection of the wild type AR with Rb or ARA70 can enhance the AR transcriptional activity to 12-fold (E2) or 3–4 fold (HF), and cotransfection of Rb and ARA$_{70}$ with AR can further enhance the AR transcriptional activity to 36-fold (E2 or 12-fold (HF). We then extended these findings to two different AR mutants: mARt877s from a prostate cancer patient and mARe708k from a partial-androgen-insensitive patient. Similar inductions were obtained when wild type AR was replaced by mARt877s. In contrast, while similar induction was also detected in the presence of 1 nM DHT when we replace wild type AR with mARe708k, there was almost no induction by cotransfection of meAR708k with Rb and/or ARA70 in the presence of 10 nM E2 or 1 µM HF. These results indicated that Rb and ARA70 can synergistically induce the transcriptional activity of wild type AR and mAR877 in the presence of 1 nM DHT, 10 nM E2 or 1 µM HF. However, Rb and ARA70 synergistically induce the transcriptional activity of mAR708 only in the presence of 1 nM DHT, but not 10 nM E2 or 1 µM HF. The fact that Rb and ARA70 can induce transcriptional activity of both wild type AR and mutated AR that occur in many prostate tumors may also argue strongly the importance of Rb and ARA70 in normal prostate as well as prostate tumor. Also, the differential induction of DHT vs. E2/HF may suggest the position of 708 in AR may play vital role for the recognition of androgen vs anti-androgens to AR.

We also examined the effect of Rb and ARA70 on the transcriptional activity of other steroid receptors through their cognate DNA response elements [MMTV-CAT for AR, glucocorticoid receptor (GR), and progesterone receptor (PR); ERE-CAT for estrogen receptor (ER)]. Although Rb and ARA70 can synergistically induce AR transcriptional activity up to 64-fold, Rb and ARA70 can only have marginal induction on the transcriptional activity of GR, PR, and ER in DU145 cells. These results suggest that Rb and ARA70 are more specific coactivators for AR in prostate DU145 cells. However, it cannot be ruled out that possibly the assay conditions in prostate DU145 cells are particularly favorable for Rb and ARA70 to function as coactivators for AR only, and Rb and ARA70 may function as stronger coactivators for ER, PR, and GR in other cells or conditions. Failure of Rb to induce transactivation by mutant AR888, which is unable to bind androgen, suggests that while interaction between Rb and AR is androgen-independent, the AR-Rb (and AR-ARA70) complexes require a ligand for the transactivation activity.

The activity of Rb in cell cycle control is related essentially to its ability to bind to several proteins, thus modulating their activity. To date, many cellular proteins have been reported which bind to Rb (Weinberg, R. A., Cell 81:323–330 (1995)). These include a number of transcription factors, a putative regulator of ras, a nuclear structural protein, a protein phosphatase, and several protein kinases. Whether all of these proteins actually complex, and are regulated by Rb, in cells remains to be seen.

Much attention has been given to the functional interaction between Rb and transcription factors. To date, several of these factors have been shown to form complexes with Rb in cells. Such complex formation and subsequent function studies have revealed that the modulating activity of Rb can take the form of repression of transcription as with E2F (Weintraub et al., Nature 375:812–815 (1995)), or activation as with NF-IL6 (Chen et al., Proc. Natl. Acad. Sci. USA 93:465–469 (1996)) and the hBrm/BRG1 complex (Singh et al., (1995)). Here, we show that Rb can bind to AR and induce the AR transcriptional activity. To our knowledge, this is the first demonstration of a negative growth regulatory protein functioning in a positive manner, by initiating transcription via a signal transduction mechanism involving binding to a nuclear receptor. When place in the context of regulating the cell cycle and differentiation, these data suggest a previously undescribed function for Rb which underscores the importance of this protein in regulating transcription by direct binding to transcription-factor, but this protein can also regulate transcription by stimulating at least one type of signal transduction mechanism.

A relationship between Rb expression and response to endocrine therapy of human breast tumor has been suggested (Anderson et al., J. Pathology 180:65–70 (1996)). Other studies indicate that Rb gene alterations can occur in all grades and stages of prostate cancer, in localized as well as metastatic disease (Brooks et al., Prostate 26:35–39 (1995)). How Rb function may be linked to androgen-dependent status in prostate tumor progression remains unclear. One possible explanation is that Rb alteration may be a necessary event in prostate carcinogenesis for a subset of prostatic neoplasms, which may be also true for the AR expression in prostate tumors.

All publications cited in this application are incorporated by reference.

The present invention is not limited to the exemplified embodiment, but is intended to encompass all such modifications and variations as come within the scope of the following claims.

I claim:

1. An isolated polynucleotide comprising the sequence set forth in SEQ ID NO:3.

2. An isolated polynucleotide comprising a promoter capable of causing expression of a protein coding region in a cell, the promoter operably connected to a protein coding region of a polypeptide set forth in SEQ ID NO:4.

3. The isolated polynucleotide of claim 2 wherein the protein coding region comprises a sequence set forth in SEQ ID NO: 3.

4. A eukaryotic host cell comprising the isolated polynucleotide of claim 2.

5. An isolated polynucleotide encoding an ARA55 polypeptide comprising amino acids 251–444 of SEQ ID NO: 4 and a LIM motif, wherein the ARA55 polypeptide enhances the transcription activity of an Androgen Receptor.

6. The isolated polynucleotide of claim 5, wherein the ARA55 polypeptide enhances the transcription activity of an Androgen Receptor at least 4 fold.

7. The isolated polynucleotide claim 5, wherein the ARA55 polypeptide enhances the transcription activity of an Androgen Receptor at least 8 fold.

8. The isolated polynucleotide of claim 5, wherein the enhancement comprises an interaction between 17 β estradiol (E2) and a mutant Androgen Receptor.

9. The isolated polynucleotide of claim 5, wherein the enhancement comprises an interaction between hydroxyflutamide (HF) and a mutant Androgen Receptor.

10. The isolated polynucleotide of claim 5, wherein the enhancement comprises an interaction between dihydrotestosterone (DHT) and a mutant Androgen Receptor.

11. An isolated polynucleotide encoding an ARA55 polypeptide comprising amino aids 251–444 of SEQ ID NO: 4 and a protein called a LIM motif, wherein the ARA55 polypeptide enhances the transcriptional activity of a mutant Androgen Receptor.

12. The isolated polynucleotide of claim 11, wherein the enhancement comprises an interaction between 17 β estradiol (E2) and the mutant Androgen Receptor.

13. The isolated polynucleotide of claim 11, wherein the enhancement comprises an interaction between hydroxyflutamide (HF) and the mutant Androgen Receptor.

14. The isolated polynucleotide of claim 11, wherein the enhancement comprises an interaction between dihydrotestosterone (DHT) and the mutant Androgen Receptor.

15. The isolated polynucleotide of claim 11, wherein the enhancement comprises an interaction between testosterone (T) and the mutant Androgen Receptor.

16. An isolated polynucleotide encoding an ARA55 polypeptide comprising amino acids 251–444 of SEQ ID NO: 4, wherein the ARA55 polypeptide inhibits the transcription activity of an Androgen Receptor.

* * * * *

SEQUENCE LISTING

```
<160> NUMBER OF SEQ ID NOS: 12

<210> SEQ ID NO 1
<211> LENGTH: 1721
<212> TYPE: DNA
<213> ORGANISM: Homo sapien
<220> FEATURE:
<221> NAME/KEY: CDS
<222> LOCATION: (40)..(1464)
<220> FEATURE:
<221> NAME/KEY: misc_feature
<222> LOCATION: (1120)..(1452)
<223> OTHER INFORMATION: Coding sequence and polypeptide region for the
      C-terminal domain.
<220> FEATURE:
<221> NAME/KEY: misc_feature
<222> LOCATION: (697)..(834)
<223> OTHER INFORMATION: Coding sequence and polypeptide region which
      may form a cystein-rich RING finger motif.
```

```
<220> FEATURE:
<221> NAME/KEY: misc_feature
<222> LOCATION: (964)..(1089)
<223> OTHER INFORMATION: Coding sequence and polypeptide region for a
      cystein-rich B box like structure.

<400> SEQUENCE: 1
ggtctctggt ctccctctc tgagcactct gaggtcctt atg tcg tca gaa gat         54
                                           Met Ser Ser Glu Asp
                                           1               5 cga gaa gct cag gag gat gaa ttg ctg gcc ctg gca agt att tac gat       102
Arg Glu Ala Gln Glu Asp Glu Leu Leu Ala Leu Ala Ser Ile Tyr Asp
            10                  15                  20 gga gat gaa ttt aga aaa gca gag tct gtc caa ggt gga gaa acc agg       150
Gly Asp Glu Phe Arg Lys Ala Glu Ser Val Gln Gly Gly Glu Thr Arg
            25                  30                  35 atc tat ttg gat ttg cca cag aat ttc aag ata ttt gtg agc ggc aat       198
Ile Tyr Leu Asp Leu Pro Gln Asn Phe Lys Ile Phe Val Ser Gly Asn
        40                  45                  50 tca aat gag tgt ctc cag aat agt ggc ttt gaa tac acc att tgc ttt       246
Ser Asn Glu Cys Leu Gln Asn Ser Gly Phe Glu Tyr Thr Ile Cys Phe
    55                  60                  65 ctg cct cca ctt gtg ctg aac ttt gaa ctg cca cca gat tat cca tcc       294
Leu Pro Pro Leu Val Leu Asn Phe Glu Leu Pro Pro Asp Tyr Pro Ser
70                  75                  80                  85 tct tcc cca cct tca ttc aca ctt agt ggc aaa tgg ctg tca cca act       342
Ser Ser Pro Pro Ser Phe Thr Leu Ser Gly Lys Trp Leu Ser Pro Thr
                90                  95                  100 cag cta tct gct cta tgc aag cac tta gac aac cta tgg gaa gaa cac       390
Gln Leu Ser Ala Leu Cys Lys His Leu Asp Asn Leu Trp Glu Glu His
            105                 110                 115 cgt ggc agc gtg gtc ctg ttt gcc tgg atg caa ttt ctt aag gaa gag       438
Arg Gly Ser Val Val Leu Phe Ala Trp Met Gln Phe Leu Lys Glu Glu
            120                 125                 130 acc cta gca tac ttg aat att gtc tct cct ttt gag ctc aag att ggt       486
Thr Leu Ala Tyr Leu Asn Ile Val Ser Pro Phe Glu Leu Lys Ile Gly
        135                 140                 145 tct cag aaa aaa gtg cag aga agg aca gct caa gct tct ccc aac aca       534
Ser Gln Lys Lys Val Gln Arg Arg Thr Ala Gln Ala Ser Pro Asn Thr
150                 155                 160                 165 gag cta gat ttt gga gga gct gct gga tct gat gta gac caa gag gaa       582
Glu Leu Asp Phe Gly Gly Ala Ala Gly Ser Asp Val Asp Gln Glu Glu
                170                 175                 180 att gtg gat gag aga gca gtg cag gat gtg gaa tca ctg tca aat ctg       630
Ile Val Asp Glu Arg Ala Val Gln Asp Val Glu Ser Leu Ser Asn Leu
            185                 190                 195 atc cag gaa atc ttg gac ttt gat caa gct cag cag ata aaa tgc ttt       678
Ile Gln Glu Ile Leu Asp Phe Asp Gln Ala Gln Gln Ile Lys Cys Phe
            200                 205                 210 aat agt aaa ttg ttc ctg tgc agt atc tgt ttc tgt gag aag ctg ggt       726
Asn Ser Lys Leu Phe Leu Cys Ser Ile Cys Phe Cys Glu Lys Leu Gly
        215                 220                 225 agt gaa tgc atg tac ttc ttg gag tgc agg cat gtg tac tgc aaa gcc       774
Ser Glu Cys Met Tyr Phe Leu Glu Cys Arg His Val Tyr Cys Lys Ala
230                 235                 240                 245 tgt ctg aag gac tac ttt gaa atc cag atc aga gat ggc cag gtt caa       822
Cys Leu Lys Asp Tyr Phe Glu Ile Gln Ile Arg Asp Gly Gln Val Gln
                250                 255                 260 tgc ctc aac tgc cca gaa cca aag tgc cct tcg gtg gcc act cct ggt       870
Cys Leu Asn Cys Pro Glu Pro Lys Cys Pro Ser Val Ala Thr Pro Gly
            265                 270                 275
```

-continued

| | |
|---|---|
| cag gtc aaa gag tta gtg gaa gca gag tta ttt gcc cgt tat gac cgc<br>Gln Val Lys Glu Leu Val Glu Ala Glu Leu Phe Ala Arg Tyr Asp Arg<br>     280                   285                    290 | 918 |
| ctt ctc ctc cag tcc tcc ttg gac ctg atg gca gat gtg gtg tac tgc<br>Leu Leu Leu Gln Ser Ser Leu Asp Leu Met Ala Asp Val Val Tyr Cys<br>295                     300                   305 | 966 |
| ccc cgg ccg tgc tgc cag ctg cct gtg atg cag gaa cct ggc tgc acc<br>Pro Arg Pro Cys Cys Gln Leu Pro Val Met Gln Glu Pro Gly Cys Thr<br>310                     315                   320                325 | 1014 |
| atg ggt atc tgc tcc agc tgc aat ttt gcc ttc tgt act ttg tgc agg<br>Met Gly Ile Cys Ser Ser Cys Asn Phe Ala Phe Cys Thr Leu Cys Arg<br>                330                        335                340 | 1062 |
| ttg acc tac cat ggg gtc tcc cca tgt aag gtg act gca gag aaa tta<br>Leu Thr Tyr His Gly Val Ser Pro Cys Lys Val Thr Ala Glu Lys Leu<br>345                     350                   355 | 1110 |
| atg gac tta cga aat gaa tac ctg caa gcg gat gag gct aat aaa aga<br>Met Asp Leu Arg Asn Glu Tyr Leu Gln Ala Asp Glu Ala Asn Lys Arg<br>360                     365                   370 | 1158 |
| ctt ttg gat caa agg tat ggt aag aga gtg att cag aag gca ctg gaa<br>Leu Leu Asp Gln Arg Tyr Gly Lys Arg Val Ile Gln Lys Ala Leu Glu<br>375                     380                   385 | 1206 |
| gag atg gaa agt aag gag tgg cta gag aag aac tca aag agc tgc cca<br>Glu Met Glu Ser Lys Glu Trp Leu Glu Lys Asn Ser Lys Ser Cys Pro<br>390                     395                   400                405 | 1254 |
| tgt tgt gga act ccc ata gag aaa tta gac gga tgt aac aag atg aca<br>Cys Cys Gly Thr Pro Ile Glu Lys Leu Asp Gly Cys Asn Lys Met Thr<br>                410                        415                420 | 1302 |
| tgt act ggc tgt atg caa tat ttc tgt tgg att tgc atg ggt tct ctc<br>Cys Thr Gly Cys Met Gln Tyr Phe Cys Trp Ile Cys Met Gly Ser Leu<br>                     425                       430                   435 | 1350 |
| tct aga gca aac cct tac aaa cat ttc aat gac cct ggt tca cca tgt<br>Ser Arg Ala Asn Pro Tyr Lys His Phe Asn Asp Pro Gly Ser Pro Cys<br>              440                       445                   450 | 1398 |
| ttt aac cgg ctg ttt tat gct gtg gat gtt gac gac gat att tgg gaa<br>Phe Asn Arg Leu Phe Tyr Ala Val Asp Val Asp Asp Asp Ile Trp Glu<br>455                     460                   465 | 1446 |
| gat gag gta gaa gac tag ttaactactg ctcaagatat ttaactactg<br>Asp Glu Val Glu Asp<br>470                   475 | 1494 |
| ctcaagatat ggaagtggat tgttttttccc taatcttccg tcaagtacac aaagtaactt | 1554 |
| tgcgggatat ttagggtact attcattcac tcttcctgcg tagaagatat ggaagaacga | 1614 |
| ggtttatatt ttcatgtggt actactgaag aaggtgcatt gatacatttt taaatgtaag | 1674 |
| ttgagaaaaa tttataagcc aaaggttcag aaaattaaac tacagaa | 1721 |

<210> SEQ ID NO 2
<211> LENGTH: 474
<212> TYPE: PRT
<213> ORGANISM: Homo sapien
<400> SEQUENCE: 2

Met Ser Ser Glu Asp Arg Glu Ala Gln Glu Asp Glu Leu Leu Ala Leu
1               5                    10                   15

Ala Ser Ile Tyr Asp Gly Asp Glu Phe Arg Lys Ala Glu Ser Val Gln
                  20                    25                   30

Gly Gly Glu Thr Arg Ile Tyr Leu Asp Leu Pro Gln Asn Phe Lys Ile
             35                    40                    45

Phe Val Ser Gly Asn Ser Asn Glu Cys Leu Gln Asn Ser Gly Phe Glu
50                       55                    60

```
Tyr Thr Ile Cys Phe Leu Pro Pro Leu Val Leu Asn Phe Glu Leu Pro
 65                  70                  75                  80

Pro Asp Tyr Pro Ser Ser Pro Ser Phe Thr Leu Ser Gly Lys
             85                  90                  95

Trp Leu Ser Pro Thr Gln Leu Ser Ala Leu Cys Lys His Leu Asp Asn
             100                 105                 110

Leu Trp Glu Glu His Arg Gly Ser Val Val Leu Phe Ala Trp Met Gln
         115                 120                 125

Phe Leu Lys Glu Glu Thr Leu Ala Tyr Leu Asn Ile Val Ser Pro Phe
         130                 135                 140

Glu Leu Lys Ile Gly Ser Gln Lys Lys Val Gln Arg Arg Thr Ala Gln
145                 150                 155                 160

Ala Ser Pro Asn Thr Glu Leu Asp Phe Gly Ala Ala Gly Ser Asp
             165                 170                 175

Val Asp Gln Glu Glu Ile Val Asp Glu Arg Ala Val Gln Asp Val Glu
             180                 185                 190

Ser Leu Ser Asn Leu Ile Gln Glu Ile Leu Asp Phe Asp Gln Ala Gln
         195                 200                 205

Gln Ile Lys Cys Phe Asn Ser Lys Leu Phe Leu Cys Ser Ile Cys Phe
    210                 215                 220

Cys Glu Lys Leu Gly Ser Glu Cys Met Tyr Phe Leu Glu Cys Arg His
225                 230                 235                 240

Val Tyr Cys Lys Ala Cys Leu Lys Asp Tyr Phe Glu Ile Gln Ile Arg
             245                 250                 255

Asp Gly Gln Val Gln Cys Leu Asn Cys Pro Glu Pro Lys Cys Pro Ser
             260                 265                 270

Val Ala Thr Pro Gly Gln Val Lys Glu Leu Val Glu Ala Glu Leu Phe
             275                 280                 285

Ala Arg Tyr Asp Arg Leu Leu Leu Gln Ser Ser Leu Asp Leu Met Ala
         290                 295                 300

Asp Val Val Tyr Cys Pro Arg Pro Cys Cys Gln Leu Pro Val Met Gln
305                 310                 315                 320

Glu Pro Gly Cys Thr Met Gly Ile Cys Ser Ser Cys Asn Phe Ala Phe
             325                 330                 335

Cys Thr Leu Cys Arg Leu Thr Tyr His Gly Val Ser Pro Cys Lys Val
             340                 345                 350

Thr Ala Glu Lys Leu Met Asp Leu Arg Asn Glu Tyr Leu Gln Ala Asp
         355                 360                 365

Glu Ala Asn Lys Arg Leu Leu Asp Gln Arg Tyr Gly Lys Arg Val Ile
    370                 375                 380

Gln Lys Ala Leu Glu Glu Met Glu Ser Lys Glu Trp Leu Glu Lys Asn
385                 390                 395                 400

Ser Lys Ser Cys Pro Cys Cys Gly Thr Pro Ile Glu Lys Leu Asp Gly
             405                 410                 415

Cys Asn Lys Met Thr Cys Thr Gly Cys Met Gln Tyr Phe Cys Trp Ile
             420                 425                 430

Cys Met Gly Ser Leu Ser Arg Ala Asn Pro Tyr Lys His Phe Asn Asp
             435                 440                 445

Pro Gly Ser Pro Cys Phe Asn Arg Leu Phe Tyr Ala Val Asp Val Asp
             450                 455                 460

Asp Asp Ile Trp Glu Asp Glu Val Glu Asp
465                 470
```

```
<210> SEQ ID NO 3
<211> LENGTH: 1335
<212> TYPE: DNA
<213> ORGANISM: Homo sapien
<220> FEATURE:
<221> NAME/KEY: CDS
<222> LOCATION: (1)..(1335)
<220> FEATURE:
<221> NAME/KEY: misc_feature
<222> LOCATION: (750)..(1332)
<223> OTHER INFORMATION: Coding sequence and polypeptide region for the
      C-terminal binding domain
<220> FEATURE:
<221> NAME/KEY: misc_feature
<222> LOCATION: (631)..(783)
<223> OTHER INFORMATION: Coding sequence and polypeptide region for a
      cystein rich LIM motif
<220> FEATURE:
<221> NAME/KEY: misc_feature
<222> LOCATION: (808)..(996)
<223> OTHER INFORMATION: Coding sequence and polypeptide region for a
      cystein rich LIM motif
<220> FEATURE:
<221> NAME/KEY: misc_feature
<222> LOCATION: (985)..(1137)
<223> OTHER INFORMATION: Coding sequence and polypeptide region for a
      cystein rich LIM motif
<220> FEATURE:
<221> NAME/KEY: misc_feature
<222> LOCATION: (1162)..(1314)
<223> OTHER INFORMATION: Coding sequence and polypeptide region for a
      cystein rich LIM motif

<400> SEQUENCE: 3 atg cca agg tca ggg gct ccc aaa gag cgc cct gcg gag cct ctc acc      48
Met Pro Arg Ser Gly Ala Pro Lys Glu Arg Pro Ala Glu Pro Leu Thr
 1               5                  10                  15 cct ccc cca tcc tat ggc cac cag cca aca ggg cag tct ggg gag tct      96
Pro Pro Pro Ser Tyr Gly His Gln Pro Thr Gly Gln Ser Gly Glu Ser
             20                  25                  30 tca gga gcc tcg ggg gac aag gac cac ctg tac agc acg gta tgc aag     144
Ser Gly Ala Ser Gly Asp Lys Asp His Leu Tyr Ser Thr Val Cys Lys
         35                  40                  45 cct cgg tcc cca aag cct gca gcc cgg gcc gcc cct cca ttc tcc tct     192
Pro Arg Ser Pro Lys Pro Ala Ala Pro Ala Ala Pro Pro Phe Ser Ser
     50                  55                  60 tcc agc ggt gtc ttg ggt acc ggg ctc tgt gag cta gat cgg ttg ctt     240
Ser Ser Gly Val Leu Gly Thr Gly Leu Cys Glu Leu Asp Arg Leu Leu
 65                  70                  75                  80 cag gaa ctt aat gcc act cag ttc aac atc aca gat gaa atc atg tct     288
Gln Glu Leu Asn Ala Thr Gln Phe Asn Ile Thr Asp Glu Ile Met Ser
                 85                  90                  95 cag ttc cca tct agc aag gtg gct tca gga gag cag aag gag gac cag     336
Gln Phe Pro Ser Ser Lys Val Ala Ser Gly Glu Gln Lys Glu Asp Gln
            100                 105                 110 tct gaa gat aag aaa aga ccc agc ctc cct tcc agc ccg tct cct ggc     384
Ser Glu Asp Lys Lys Arg Pro Ser Leu Pro Ser Ser Pro Ser Pro Gly
        115                 120                 125 ctc cca aag gct tct gcc acc tca gcc act ctg gag ctg gat aga ctg     432
Leu Pro Lys Ala Ser Ala Thr Ser Ala Thr Leu Glu Leu Asp Arg Leu
    130                 135                 140 atg gcc tca ctc cct gac ttc cgc gtt caa aac cat ctt cca gcc tct     480
Met Ala Ser Leu Pro Asp Phe Arg Val Gln Asn His Leu Pro Ala Ser
145                 150                 155                 160 ggg cca act cag cca ccg gtg gtg agc tcc aca aat gag ggc tcc cca     528
Gly Pro Thr Gln Pro Pro Val Val Ser Ser Thr Asn Glu Gly Ser Pro
                165                 170                 175
```

| | | |
|---|---|---|
| tcc cca cca gag ccg act gca aag ggc agc cta gac acc atg ctg ggg<br>Ser Pro Pro Glu Pro Thr Ala Lys Gly Ser Leu Asp Thr Met Leu Gly<br>180 185 190 | 576 | |
| ctg ctg cag tcc gac ctc agc cgc cgg ggt gtt ccc acc cag gcc aaa<br>Leu Leu Gln Ser Asp Leu Ser Arg Arg Gly Val Pro Thr Gln Ala Lys<br>195 200 205 | 624 | |
| ggc ctc tgt ggc tcc tgc aat aaa cct att gct ggg caa gtg gtg acg<br>Gly Leu Cys Gly Ser Cys Asn Lys Pro Ile Ala Gly Gln Val Val Thr<br>210 215 220 | 672 | |
| gct ctg ggc cgc gcc tgg cac ccc gag cac ttc gtt tgc gga ggc tgt<br>Ala Leu Gly Arg Ala Trp His Pro Glu His Phe Val Cys Gly Gly Cys<br>225 230 235 240 | 720 | |
| tcc acc gcc ctg gga ggc agc agc ttc ttc gag aag gat gga gcc ccc<br>Ser Thr Ala Leu Gly Gly Ser Ser Phe Phe Glu Lys Asp Gly Ala Pro<br>245 250 255 | 768 | |
| ttc tgc ccc gag tgc tac ttt gag cgc ttc tcg cca aga tgt ggc ttc<br>Phe Cys Pro Glu Cys Tyr Phe Glu Arg Phe Ser Pro Arg Cys Gly Phe<br>260 265 270 | 816 | |
| tgc aac cag ccc atc cga cac aag atg gtg acc gcc ttg ggc act cac<br>Cys Asn Gln Pro Ile Arg His Lys Met Val Thr Ala Leu Gly Thr His<br>275 280 285 | 864 | |
| tgg cac cca gag cat ttc tgc tgc gtc agt tgc ggg gag ccc ttc gga<br>Trp His Pro Glu His Phe Cys Cys Val Ser Cys Gly Glu Pro Phe Gly<br>290 295 300 | 912 | |
| gat gag ggt ttc cac gag cgc gag ggc cgc ccc tac tgc cgc cgg gac<br>Asp Glu Gly Phe His Glu Arg Glu Gly Arg Pro Tyr Cys Arg Arg Asp<br>305 310 315 320 | 960 | |
| ttc ctg cag ctg ttc gcc ccg cgc tgc cag ggc tgc cag ggc ccc atc<br>Phe Leu Gln Leu Phe Ala Pro Arg Cys Gln Gly Cys Gln Gly Pro Ile<br>325 330 335 | 1008 | |
| ctg gat aac tac atc tcg gcg ctc agc ctg ctc tgg cac ccg gac tgt<br>Leu Asp Asn Tyr Ile Ser Ala Leu Ser Leu Leu Trp His Pro Asp Cys<br>340 345 350 | 1056 | |
| ttc gtc tgc agg gaa tgc ttc gcg ccc ttc tcg gga ggc agc ttt ttc<br>Phe Val Cys Arg Glu Cys Phe Ala Pro Phe Ser Gly Gly Ser Phe Phe<br>355 360 365 | 1104 | |
| gag cac gag ggc cgc ccg ttg tgc gag aac cac ttc cac gca cga cgc<br>Glu His Glu Gly Arg Pro Leu Cys Glu Asn His Phe His Ala Arg Arg<br>370 375 380 | 1152 | |
| ggc tcg ctg tgc ccc acg tgt ggc ctc cct gtg acc ggc cgc tgc gtg<br>Gly Ser Leu Cys Pro Thr Cys Gly Leu Pro Val Thr Gly Arg Cys Val<br>385 390 395 400 | 1200 | |
| tcg gcc ctg ggt cgc cgc ttc cac ccg gac cac ttc gca tgc acc ttc<br>Ser Ala Leu Gly Arg Arg Phe His Pro Asp His Phe Ala Cys Thr Phe<br>405 410 415 | 1248 | |
| tgc ctg cgc ccg ctc acc aag ggg tcc ttc cag gag cgc gcc ggc aag<br>Cys Leu Arg Pro Leu Thr Lys Gly Ser Phe Gln Glu Arg Ala Gly Lys<br>420 425 430 | 1296 | |
| ccc tac tgc cag ccc tgc ttc ctg aag ctc ttc ggc tga<br>Pro Tyr Cys Gln Pro Cys Phe Leu Lys Leu Phe Gly<br>435 440 445 | 1335 | |

<210> SEQ ID NO 4
<211> LENGTH: 444
<212> TYPE: PRT
<213> ORGANISM: Homo sapien

```
<400> SEQUENCE: 4

Met Pro Arg Ser Gly Ala Pro Lys Glu Arg Pro Ala Glu Pro Leu Thr
 1               5                  10                  15

Pro Pro Pro Ser Tyr Gly His Gln Pro Thr Gly Gln Ser Gly Glu Ser
             20                  25                  30

Ser Gly Ala Ser Gly Asp Lys Asp His Leu Tyr Ser Thr Val Cys Lys
         35                  40                  45

Pro Arg Ser Pro Lys Pro Ala Ala Pro Ala Ala Pro Pro Phe Ser Ser
     50                  55                  60

Ser Ser Gly Val Leu Gly Thr Gly Leu Cys Glu Leu Asp Arg Leu Leu
 65                  70                  75                  80

Gln Glu Leu Asn Ala Thr Gln Phe Asn Ile Thr Asp Glu Ile Met Ser
                 85                  90                  95

Gln Phe Pro Ser Ser Lys Val Ala Ser Gly Glu Gln Lys Glu Asp Gln
            100                 105                 110

Ser Glu Asp Lys Lys Arg Pro Ser Leu Pro Ser Ser Pro Ser Pro Gly
            115                 120                 125

Leu Pro Lys Ala Ser Ala Thr Ser Ala Thr Leu Glu Leu Asp Arg Leu
130                 135                 140

Met Ala Ser Leu Pro Asp Phe Arg Val Gln Asn His Leu Pro Ala Ser
145                 150                 155                 160

Gly Pro Thr Gln Pro Pro Val Val Ser Ser Thr Asn Glu Gly Ser Pro
                165                 170                 175

Ser Pro Pro Glu Pro Thr Ala Lys Gly Ser Leu Asp Thr Met Leu Gly
            180                 185                 190

Leu Leu Gln Ser Asp Leu Ser Arg Arg Gly Val Pro Thr Gln Ala Lys
            195                 200                 205

Gly Leu Cys Gly Ser Cys Asn Lys Pro Ile Ala Gly Gln Val Val Thr
            210                 215                 220

Ala Leu Gly Arg Ala Trp His Pro Glu His Phe Val Cys Gly Gly Cys
225                 230                 235                 240

Ser Thr Ala Leu Gly Gly Ser Ser Phe Glu Lys Asp Gly Ala Pro
                245                 250                 255

Phe Cys Pro Glu Cys Tyr Phe Glu Arg Phe Ser Pro Arg Cys Gly Phe
            260                 265                 270

Cys Asn Gln Pro Ile Arg His Lys Met Val Thr Ala Leu Gly Thr His
            275                 280                 285

Trp His Pro Glu His Phe Cys Cys Val Ser Cys Gly Glu Pro Phe Gly
            290                 295                 300

Asp Glu Gly Phe His Glu Arg Glu Gly Arg Pro Tyr Cys Arg Arg Asp
305                 310                 315                 320

Phe Leu Gln Leu Phe Ala Pro Arg Cys Gln Gly Cys Gln Gly Pro Ile
            325                 330                 335

Leu Asp Asn Tyr Ile Ser Ala Leu Ser Leu Leu Trp His Pro Asp Cys
            340                 345                 350

Phe Val Cys Arg Glu Cys Phe Ala Pro Phe Ser Gly Gly Ser Phe Phe
            355                 360                 365

Glu His Glu Gly Arg Pro Leu Cys Glu Asn His Phe His Ala Arg Arg
            370                 375                 380

Gly Ser Leu Cys Pro Thr Cys Gly Leu Pro Val Thr Gly Arg Cys Val
385                 390                 395                 400

Ser Ala Leu Gly Arg Arg Phe His Pro Asp His Phe Ala Cys Thr Phe
                405                 410                 415
```

```
Cys Leu Arg Pro Leu Thr Lys Gly Ser Phe Gln Glu Arg Ala Gly Lys
            420                 425                 430
Pro Tyr Cys Gln Pro Cys Phe Leu Lys Leu Phe Gly
        435                 440

<210> SEQ ID NO 5
<211> LENGTH: 1566
<212> TYPE: DNA
<213> ORGANISM: Homo sapien
<220> FEATURE:
<221> NAME/KEY: CDS
<222> LOCATION: (25)..(675)
<220> FEATURE:
<221> NAME/KEY: 3'UTR
<222> LOCATION: (676)..(1566)
<220> FEATURE:
<221> NAME/KEY: 5'UTR
<222> LOCATION: (1)..(24)

<400> SEQUENCE: 5
ggcgcttctg gaaggaacgc cgcg atg gct gcg cag gga gag ccc cag gtc      51
                          Met Ala Ala Gln Gly Glu Pro Gln Val
                            1               5 cag ttc aaa ctt gta ttg gtt ggt gat ggt ggt act gga aaa acg acc    99
Gln Phe Lys Leu Val Leu Val Gly Asp Gly Gly Thr Gly Lys Thr Thr
 10              15                  20                  25 ttc gtg aaa cgt cat ttg act ggt gaa ttt gag aag aag tat gta gcc   147
Phe Val Lys Arg His Leu Thr Gly Glu Phe Glu Lys Lys Tyr Val Ala
                 30                  35                  40 acc ttg ggt gtt gag gtt cat ccc cta gtg ttc cac acc aac aga gga   195
Thr Leu Gly Val Glu Val His Pro Leu Val Phe His Thr Asn Arg Gly
             45                  50                  55 cct att aag ttc aat gta tgg gac aca gcc ggc cag gag aaa ttc ggt   243
Pro Ile Lys Phe Asn Val Trp Asp Thr Ala Gly Gln Glu Lys Phe Gly
         60                  65                  70 gga ctg aga gat ggc tat tat atc caa gcc cag tgt gcc atc ata atg   291
Gly Leu Arg Asp Gly Tyr Tyr Ile Gln Ala Gln Cys Ala Ile Ile Met
     75                  80                  85 ttt gat gta aca tcg aga gtt act tac aag aat gtg cct aac tgg cat   339
Phe Asp Val Thr Ser Arg Val Thr Tyr Lys Asn Val Pro Asn Trp His
 90                  95                 100                 105 aga gat ctg gta cga gtg tgt gaa aac atc ccc att gtg ttg tgt ggc   387
Arg Asp Leu Val Arg Val Cys Glu Asn Ile Pro Ile Val Leu Cys Gly
                110                 115                 120 aac aaa gtg gat att aag gac agg aaa gtg aag gcg aaa tcc att gtc   435
Asn Lys Val Asp Ile Lys Asp Arg Lys Val Lys Ala Lys Ser Ile Val
            125                 130                 135 ttc cac cga aag aag aat ctt cag tac tac gac att tct gcc aaa agt   483
Phe His Arg Lys Lys Asn Leu Gln Tyr Tyr Asp Ile Ser Ala Lys Ser
        140                 145                 150 aac tac aac ttt gaa aag ccc ttc ctc tgg ctt gct agg aag ctc att   531
Asn Tyr Asn Phe Glu Lys Pro Phe Leu Trp Leu Ala Arg Lys Leu Ile
    155                 160                 165 gga gac cct aac ttg gaa ttt gtt gcc atg cct gct ctc gcc cca cca   579
Gly Asp Pro Asn Leu Glu Phe Val Ala Met Pro Ala Leu Ala Pro Pro
170                 175                 180                 185 gaa gtt gtc atg gac cca gct ttg gca gca cag tat gag cac gac tta   627
Glu Val Val Met Asp Pro Ala Leu Ala Ala Gln Tyr Glu His Asp Leu
                190                 195                 200 gag gtt gct cag aca act gct ctc ccg gat gag gat gat gac ctg tga   675
Glu Val Ala Gln Thr Thr Ala Leu Pro Asp Glu Asp Asp Asp Leu
            205                 210                 215
```

-continued

```
gaatgaagct ggagcccagc gtcagaagtc tagtttttata ggcagctgtc ctgtgatgtc    735
agcggtgcag cgtgtgtgcc acctcattat tatctagcta agcggaacat gtgctttatc    795
tgtgggatgc tgaaggagat gagtgggctt cggagtgaat gtggcagttt aaaaaataac    855
ttcattgttt ggacctgcat atttagctgt ttggacgcag ttgattcctt gagtttcata    915
tataagactg ctgcagtcac atcacaatat tcagtggtga atcttgttt gttactgtca     975
ttcccattcc ttttctttag aatcagaata aagttgtatt tcaaatatct aagcaagtga   1035
actcatccct tgtttataaa tagcatttgg aaaccactaa agtagggaag ttttatgcca   1095
tgttaatatt tgaattgcct tgcttttatc acttaatttg aaatctattg ggttaatttc   1155
tccctatgtt tattttttgta catttgagcc atgtcacaca aactgatgat gacaggtcag  1215
cagtattcta tttggttaga agggttacat ggtgtaaata ttagtgcagt taagctaaag   1275
cagtgtttgc tccaccttca tattggctag gtagggtcac ctagggaagc acttgctcaa   1335
aatctgtgac ctgtcagaat aaaaatgtgg tttgtacata tcaaatagat attttaaggg   1395
taatattttc ttttatggca aaagtaatca tgttttaatg tagaacctca aacaggatgg   1455
aacatcagtg gatggcagga ggttgggaat tcttgctgtt aaaaataatt acaaattttg   1515
cacttttgt ttgaatgtta gatgcttagt gtgaagttga tacgcaagcc g             1566
```

<210> SEQ ID NO 6
<211> LENGTH: 216
<212> TYPE: PRT
<213> ORGANISM: Homo sapien

<400> SEQUENCE: 6

```
Met Ala Ala Gln Gly Glu Pro Gln Val Gln Phe Lys Leu Val Leu Val
  1               5                  10                  15

Gly Asp Gly Gly Thr Gly Lys Thr Thr Phe Val Lys Arg His Leu Thr
             20                  25                  30

Gly Glu Phe Glu Lys Lys Tyr Val Ala Thr Leu Gly Val Glu Val His
         35                  40                  45

Pro Leu Val Phe His Thr Asn Arg Gly Pro Ile Lys Phe Asn Val Trp
     50                  55                  60

Asp Thr Ala Gly Gln Glu Lys Phe Gly Gly Leu Arg Asp Gly Tyr Tyr
 65                  70                  75                  80

Ile Gln Ala Gln Cys Ala Ile Ile Met Phe Asp Val Thr Ser Arg Val
                 85                  90                  95

Thr Tyr Lys Asn Val Pro Asn Trp His Arg Asp Leu Val Arg Val Cys
            100                 105                 110

Glu Asn Ile Pro Ile Val Leu Cys Gly Asn Lys Val Asp Ile Lys Asp
        115                 120                 125

Arg Lys Val Lys Ala Lys Ser Ile Val Phe His Arg Lys Lys Asn Leu
    130                 135                 140

Gln Tyr Tyr Asp Ile Ser Ala Lys Ser Asn Tyr Asn Phe Glu Lys Pro
145                 150                 155                 160

Phe Leu Trp Leu Ala Arg Lys Leu Ile Gly Asp Pro Asn Leu Glu Phe
                165                 170                 175

Val Ala Met Pro Ala Leu Ala Pro Pro Glu Val Val Met Asp Pro Ala
            180                 185                 190

Leu Ala Ala Gln Tyr Glu His Asp Leu Glu Val Ala Gln Thr Thr Ala
        195                 200                 205

Leu Pro Asp Glu Asp Asp Asp Leu
    210                 215
```

-continued

```
<210> SEQ ID NO 7
<211> LENGTH: 4839
<212> TYPE: DNA
<213> ORGANISM: Homo sapien
<220> FEATURE:
<221> NAME/KEY: CDS
<222> LOCATION: (138)..(2924)

<400> SEQUENCE: 7
tccggttttt ctcaggggac gttgaaatta ttttttgtaac gggagtcggg agaggacggg      60
gcgtgccccg cgtgcgcgcg cgtcgtcctc cccggcgctc ctccacagct cgctggctcc     120
cgccgcggaa aggcgtc atg ccg ccc aaa acc ccc cga aaa acg gcc gcc        170
                    Met Pro Pro Lys Thr Pro Arg Lys Thr Ala Ala
                     1               5                  10 acc gcc gcc gct gcc gcc gcg gaa ccc ccg gca ccg ccg ccg ccc            218
Thr Ala Ala Ala Ala Ala Ala Glu Pro Pro Ala Pro Pro Pro Pro
                 15                  20                  25 cct cct gag gag gac cca gag cag gac agc ggc ccg gag gac ctg cct       266
Pro Pro Glu Glu Asp Pro Glu Gln Asp Ser Gly Pro Glu Asp Leu Pro
             30                  35                  40 ctc gtc agg ctt gag ttt gaa gaa aca gaa gaa cct gat ttt act gca       314
Leu Val Arg Leu Glu Phe Glu Glu Thr Glu Glu Pro Asp Phe Thr Ala
         45                  50                  55 tta tgt cag aaa tta aag ata cca gat cat gtc aga gag aga gct tgg       362
Leu Cys Gln Lys Leu Lys Ile Pro Asp His Val Arg Glu Arg Ala Trp
 60                  65                  70                  75 tta act tgg gag aaa gtt tca tct gtg gat gga gta ttg gga ggt tat       410
Leu Thr Trp Glu Lys Val Ser Ser Val Asp Gly Val Leu Gly Gly Tyr
                 80                  85                  90 att caa aag aaa aag gaa ctg tgg gga atc tgt atc ttt att gca gca       458
Ile Gln Lys Lys Lys Glu Leu Trp Gly Ile Cys Ile Phe Ile Ala Ala
             95                 100                 105 gtt gac cta gat gag atg tcg ttc act ttt act gag cta cag aaa aac       506
Val Asp Leu Asp Glu Met Ser Phe Thr Phe Thr Glu Leu Gln Lys Asn
         110                 115                 120 ata gaa atc agt gtc cat aaa ttc ttt aac tta cta aaa gaa att gat       554
Ile Glu Ile Ser Val His Lys Phe Phe Asn Leu Leu Lys Glu Ile Asp
     125                 130                 135 acc agt acc aaa gtt gat aat gct atg tca aga ctg ttg aag aag tat       602
Thr Ser Thr Lys Val Asp Asn Ala Met Ser Arg Leu Leu Lys Lys Tyr
140                 145                 150                 155 gat gta ttg ttt gca ctc ttc agc aaa ttg gaa agg aca tgt gaa ctt       650
Asp Val Leu Phe Ala Leu Phe Ser Lys Leu Glu Arg Thr Cys Glu Leu
                 160                 165                 170 ata tat ttg aca caa ccc agc agt tcg ata tct act gaa ata aat tct       698
Ile Tyr Leu Thr Gln Pro Ser Ser Ser Ile Ser Thr Glu Ile Asn Ser
             175                 180                 185 gca ttg gtg cta aaa gtt tct tgg atc aca ttt tta tta gct aaa ggg       746
Ala Leu Val Leu Lys Val Ser Trp Ile Thr Phe Leu Leu Ala Lys Gly
         190                 195                 200 gaa gta tta caa atg gaa gat gat ctg gtg att tca ttt cag tta atg       794
Glu Val Leu Gln Met Glu Asp Asp Leu Val Ile Ser Phe Gln Leu Met
     205                 210                 215 cta tgt gtc ctt gac tat ttt att aaa ctc tca cct ccc atg ttg ctc       842
Leu Cys Val Leu Asp Tyr Phe Ile Lys Leu Ser Pro Pro Met Leu Leu
220                 225                 230                 235 aaa gaa cca tat aaa aca gct gtt ata ccc att aat ggt tca cct cga       890
Lys Glu Pro Tyr Lys Thr Ala Val Ile Pro Ile Asn Gly Ser Pro Arg
                 240                 245                 250
```

```
aca ccc agg cga ggt cag aac agg agt gca cgg ata gca aaa caa cta      938
Thr Pro Arg Arg Gly Gln Asn Arg Ser Ala Arg Ile Ala Lys Gln Leu
        255                 260                 265 gaa aat gat aca aga att att gaa gtt ctc tgt aaa gaa cat gaa tgt      986
Glu Asn Asp Thr Arg Ile Ile Glu Val Leu Cys Lys Glu His Glu Cys
        270                 275                 280 aat ata gat gag gtg aaa aat gtt tat ttc aaa aat ttt ata cct ttt     1034
Asn Ile Asp Glu Val Lys Asn Val Tyr Phe Lys Asn Phe Ile Pro Phe
285                 290                 295 atg aat tct ctt gga ctt gta aca tct aat gga ctt cca gag gtt gaa     1082
Met Asn Ser Leu Gly Leu Val Thr Ser Asn Gly Leu Pro Glu Val Glu
300                 305                 310                 315 aat ctt tct aaa cga tac gaa gaa att tat ctt aaa aat aaa gat cta     1130
Asn Leu Ser Lys Arg Tyr Glu Glu Ile Tyr Leu Lys Asn Lys Asp Leu
                320                 325                 330 gat gca aga tta ttt ttg gat cat gat aaa act ctt cag act gat tct     1178
Asp Ala Arg Leu Phe Leu Asp His Asp Lys Thr Leu Gln Thr Asp Ser
            335                 340                 345 ata gac agt ttt gaa aca cag aga aca cca cga aaa agt aac ctt gat     1226
Ile Asp Ser Phe Glu Thr Gln Arg Thr Pro Arg Lys Ser Asn Leu Asp
        350                 355                 360 gaa gag gtg aat gta att cct cca cac act cca gtt agg act gtt atg     1274
Glu Glu Val Asn Val Ile Pro Pro His Thr Pro Val Arg Thr Val Met
365                 370                 375 aac act atc caa caa tta atg atg att tta aat tca gca agt gat caa     1322
Asn Thr Ile Gln Gln Leu Met Met Ile Leu Asn Ser Ala Ser Asp Gln
380                 385                 390                 395 cct tca gaa aat ctg att tcc tat ttt aac aac tgc aca gtg aat cca     1370
Pro Ser Glu Asn Leu Ile Ser Tyr Phe Asn Asn Cys Thr Val Asn Pro
                400                 405                 410 aaa gaa agt ata ctg aaa aga gtg aag gat ata gga tac atc ttt aaa     1418
Lys Glu Ser Ile Leu Lys Arg Val Lys Asp Ile Gly Tyr Ile Phe Lys
            415                 420                 425 gag aaa ttt gct aaa gct gtg gga cag ggt tgt gtc gaa att gga tca     1466
Glu Lys Phe Ala Lys Ala Val Gly Gln Gly Cys Val Glu Ile Gly Ser
        430                 435                 440 cag cga tac aaa ctt gga gtt cgc ttg tat tac cga gta atg gaa tcc     1514
Gln Arg Tyr Lys Leu Gly Val Arg Leu Tyr Tyr Arg Val Met Glu Ser
        445                 450                 455 atg ctt aaa tca gaa gaa gaa cga tta tcc att caa aat ttt agc aaa     1562
Met Leu Lys Ser Glu Glu Glu Arg Leu Ser Ile Gln Asn Phe Ser Lys
460                 465                 470                 475 ctt ctg aat gac aac att ttt cat atg tct tta ttg gcg tgc gct ctt     1610
Leu Leu Asn Asp Asn Ile Phe His Met Ser Leu Leu Ala Cys Ala Leu
                480                 485                 490 gag gtt gta atg gcc aca tat agc aga agt aca tct cag aat ctt gat     1658
Glu Val Val Met Ala Thr Tyr Ser Arg Ser Thr Ser Gln Asn Leu Asp
            495                 500                 505 tct gga aca gat ttg tct ttc cca tgg att ctg aat gtg ctt aat tta     1706
Ser Gly Thr Asp Leu Ser Phe Pro Trp Ile Leu Asn Val Leu Asn Leu
        510                 515                 520 aaa gcc ttt gat ttt tac aaa gtg atc gaa agt ttt atc aaa gca gaa     1754
Lys Ala Phe Asp Phe Tyr Lys Val Ile Glu Ser Phe Ile Lys Ala Glu
        525                 530                 535 ggc aac ttg aca aga gaa atg ata aaa cat tta gaa cga tgt gaa cat     1802
Gly Asn Leu Thr Arg Glu Met Ile Lys His Leu Glu Arg Cys Glu His
540                 545                 550                 555 cga atc atg gaa tcc ctt gca tgg ctc tca gat tca cct tta ttt gat     1850
Arg Ile Met Glu Ser Leu Ala Trp Leu Ser Asp Ser Pro Leu Phe Asp
                560                 565                 570
```

```
ctt att aaa caa tca aag gac cga gaa gga cca act gat cac ctt gaa      1898
Leu Ile Lys Gln Ser Lys Asp Arg Glu Gly Pro Thr Asp His Leu Glu
        575                 580                 585 tct gct tgt cct ctt aat ctt cct ctc cag aat aat cac act gca gca      1946
Ser Ala Cys Pro Leu Asn Leu Pro Leu Gln Asn Asn His Thr Ala Ala
    590                 595                 600 gat atg tat ctt tct cct gta aga tct cca aag aaa aaa ggt tca act      1994
Asp Met Tyr Leu Ser Pro Val Arg Ser Pro Lys Lys Lys Gly Ser Thr
605                 610                 615 acg cgt gta aat tct act gca aat gca gag aca caa gca acc tca gcc      2042
Thr Arg Val Asn Ser Thr Ala Asn Ala Glu Thr Gln Ala Thr Ser Ala
620                 625                 630                 635 ttc cag acc cag aag cca ttg aaa tct acc tct ctt tca ctg ttt tat      2090
Phe Gln Thr Gln Lys Pro Leu Lys Ser Thr Ser Leu Ser Leu Phe Tyr
                640                 645                 650 aaa aaa gtg tat cgg cta gcc tat ctc cgg cta aat aca ctt tgt gaa      2138
Lys Lys Val Tyr Arg Leu Ala Tyr Leu Arg Leu Asn Thr Leu Cys Glu
            655                 660                 665 cgc ctt ctg tct gag cac cca gaa tta gaa cat atc atc tgg acc ctt      2186
Arg Leu Leu Ser Glu His Pro Glu Leu Glu His Ile Ile Trp Thr Leu
        670                 675                 680 ttc cag cac acc ctg cag aat gag tat gaa ctc atg aga gac agg cat      2234
Phe Gln His Thr Leu Gln Asn Glu Tyr Glu Leu Met Arg Asp Arg His
    685                 690                 695 ttg gac caa att atg atg tgt tcc atg tat ggc ata tgc aaa gtg aag      2282
Leu Asp Gln Ile Met Met Cys Ser Met Tyr Gly Ile Cys Lys Val Lys
700                 705                 710                 715 aat ata gac ctt aaa ttc aaa atc att gta aca gca tac aag gat ctt      2330
Asn Ile Asp Leu Lys Phe Lys Ile Ile Val Thr Ala Tyr Lys Asp Leu
                720                 725                 730 cct cat gct gtt cag gag aca ttc aaa cgt gtt ttg atc aaa gaa gag      2378
Pro His Ala Val Gln Glu Thr Phe Lys Arg Val Leu Ile Lys Glu Glu
            735                 740                 745 gag tat gat tct att ata gta ttc tat aac tcg gtc ttc atg cag aga      2426
Glu Tyr Asp Ser Ile Ile Val Phe Tyr Asn Ser Val Phe Met Gln Arg
        750                 755                 760 ctg aaa aca aat att ttg cag tat gct tcc acc agg ccc cct acc ttg      2474
Leu Lys Thr Asn Ile Leu Gln Tyr Ala Ser Thr Arg Pro Pro Thr Leu
    765                 770                 775 tca cca ata cct cac att cct cga agc cct tac aag ttt cct agt tca      2522
Ser Pro Ile Pro His Ile Pro Arg Ser Pro Tyr Lys Phe Pro Ser Ser
780                 785                 790                 795 ccc tta cgg att cct gga ggg aac atc tat att tca ccc ctg aag agt      2570
Pro Leu Arg Ile Pro Gly Gly Asn Ile Tyr Ile Ser Pro Leu Lys Ser
                800                 805                 810 cca tat aaa att tca gaa ggt ctg cca aca cca aca aaa atg act cca      2618
Pro Tyr Lys Ile Ser Glu Gly Leu Pro Thr Pro Thr Lys Met Thr Pro
            815                 820                 825 aga tca aga atc tta gta tca att ggt gaa tca ttc ggg act tct gag      2666
Arg Ser Arg Ile Leu Val Ser Ile Gly Glu Ser Phe Gly Thr Ser Glu
        830                 835                 840 aag ttc cag aaa ata aat cag atg gta tgt aac agc gac cgt gtg ctc      2714
Lys Phe Gln Lys Ile Asn Gln Met Val Cys Asn Ser Asp Arg Val Leu
    845                 850                 855 aaa aga agt gct gaa gga agc aac cct cct aaa cca ctg aaa aaa cta      2762
Lys Arg Ser Ala Glu Gly Ser Asn Pro Pro Lys Pro Leu Lys Lys Leu
860                 865                 870                 875 cgc ttt gat att gaa gga tca gat gaa gca gat gga agt aaa cat ctc      2810
Arg Phe Asp Ile Glu Gly Ser Asp Glu Ala Asp Gly Ser Lys His Leu
                880                 885                 890
```

-continued

| | | |
|---|---|---|
| cca gga gag tcc aaa ttt cag cag aaa ctg gca gaa atg act tct act<br>Pro Gly Glu Ser Lys Phe Gln Gln Lys Leu Ala Glu Met Thr Ser Thr<br>895                      900                  905 | | 2858 |
| cga aca cga atg caa aag cag aaa atg aat gat agc atg gat acc tca<br>Arg Thr Arg Met Gln Lys Gln Lys Met Asn Asp Ser Met Asp Thr Ser<br>910                      915                  920 | | 2906 |
| aac aag gaa gag aaa tga ggatctcagg accttggtgg acactgtgta<br>Asn Lys Glu Glu Lys<br>925 | | 2954 |
| cacctctgga ttcattgtct ctcacagatg tgactgtata actttcccag gttctgttta | | 3014 |
| tggccacatt taatatcttc agctctttt gtggatataa aatgtgcaga tgcaattgtt | | 3074 |
| tgggtgattc ctaagccact tgaaatgtta gtcattgtta tttatacaag attgaaaatc | | 3134 |
| ttgtgtaaat cctgccattt aaaaagttgt agcagattgt ttcctcttcc aaagtaaaat | | 3194 |
| tgctgtgctt tatggatagt aagaatggcc ctagagtggg agtcctgata acccaggcct | | 3254 |
| gtctgactac tttgccttct tttgtagcat ataggtgatg tttgctcttg tttttattaa | | 3314 |
| tttatatgta tatttttta atttaacatg aacaccctta gaaatgtgt cctatctatc | | 3374 |
| ttccaaatgc aatttgattg actgcccatt caccaaaatt atcctgaact cttctgcaaa | | 3434 |
| aatggatatt attagaaatt agaaaaaaat tactaatttt acacattaga tttatttta | | 3494 |
| ctattggaat ctgatatact gtgtgcttgt tttataaaat tttgctttta attaaataaa | | 3554 |
| agctggaagc aaagtataac catatgatac tatcatacta ctgaaacaga tttcatacct | | 3614 |
| cagaatgtaa aagaacttac tgattatttt cttcatccaa cttatgtttt taaatgagga | | 3674 |
| ttattgatag tactcttggt ttttatacca ttcagatcac tgaatttata aagtacccat | | 3734 |
| ctagtacttg aaaagtaaa gtgttctgcc agatcttagg tatagaggac cctaacacag | | 3794 |
| tatatcccaa gtgcactttc taatgtttct gggtcctgaa gaattaagat acaaattaat | | 3854 |
| tttactccat aaacagactg ttaattatag gagccttaat ttttttttca tagagatttg | | 3914 |
| tctaattgca tctcaaaatt attctgccct ccttaatttg ggaaggtttg tgttttctct | | 3974 |
| ggaatggtac atgtcttcca tgtatctttt gaactggcaa ttgtctattt atcttttatt | | 4034 |
| tttttaagtc agtatggtct aacactggca tgttcaaagc cacattattt ctagtccaaa | | 4094 |
| attacaagta atcaagggtc attatgggtt aggcattaat gtttctatct gattttgtgc | | 4154 |
| aaaagcttca aattaaaaca gctgcattag aaaagaggc gcttctcccc tcccctacac | | 4214 |
| ctaaaggtgt atttaaacta tcttgtgtga ttaacttatt tagagatgct gtaacttaaa | | 4274 |
| ataggggata tttaaggtag cttcagctag cttttaggaa aatcactttg tctaactcag | | 4334 |
| aattattttt aaaagaaat ctggtcttgt tagaaaacaa aatttatttt tgtgctcatt | | 4394 |
| taagtttcaa acttactatt ttgacagtta ttttgataac aatgacacta gaaaacttga | | 4454 |
| ctccatttca tcattgtttc tgcatgaata tcatacaaat cagttagttt ttaggtcaag | | 4514 |
| ggcttactat ttctgggtct tttgctacta agttcacatt agaattagtg ccagaatttt | | 4574 |
| aggaacttca gagatcgtgt attgagattt cttaaataat gcttcagata ttattgcttt | | 4634 |
| attgctttt tgtattggtt aaaactgtac atttaaaatt gctatgttac tatttctac | | 4694 |
| aattaatagt ttgtctattt taaaataaat tagttgttaa gagtcttaat ggtctgatgt | | 4754 |
| tgtgttcttt gtattaagta cactaatgtt ctcttttctg tctaggagaa gatagataga | | 4814 |
| agataactct cctagtatct catcc | | 4839 |

-continued

<210> SEQ ID NO 8
<211> LENGTH: 928
<212> TYPE: PRT
<213> ORGANISM: Homo sapien

<400> SEQUENCE: 8

Met Pro Pro Lys Thr Pro Arg Lys Thr Ala Thr Ala Ala Ala Ala
1               5                   10                  15

Ala Ala Glu Pro Pro Ala Pro Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
            85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
        275                 280                 285

Lys Asn Val Tyr Phe Lys Asn Phe Ile Pro Phe Met Asn Ser Leu Gly
    290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Glu Val Asn Val
        355                 360                 365

Ile Pro Pro His Thr Pro Val Arg Thr Val Met Asn Thr Ile Gln Gln
    370                 375                 380

```
                                                    -continued

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
            420                 425                 430

Ala Val Gly Gln Gly Cys Val Glu Ile Gly Ser Gln Arg Tyr Lys Leu
        435                 440                 445

Gly Val Arg Leu Tyr Tyr Arg Val Met Glu Ser Met Leu Lys Ser Glu
    450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
            500                 505                 510

Ser Phe Pro Trp Ile Leu Asn Val Leu Asn Leu Lys Ala Phe Asp Phe
        515                 520                 525

Tyr Lys Val Ile Glu Ser Phe Ile Lys Ala Glu Gly Asn Leu Thr Arg
    530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
            580                 585                 590

Asn Leu Pro Leu Gln Asn Asn His Thr Ala Ala Asp Met Tyr Leu Ser
        595                 600                 605

Pro Val Arg Ser Pro Lys Lys Lys Gly Ser Thr Thr Arg Val Asn Ser
    610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
            660                 665                 670

His Pro Glu Leu Glu His Ile Ile Trp Thr Leu Phe Gln His Thr Leu
        675                 680                 685

Gln Asn Glu Tyr Glu Leu Met Arg Asp Arg His Leu Asp Gln Ile Met
    690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Tyr Asp Ser Ile
            740                 745                 750

Ile Val Phe Tyr Asn Ser Val Phe Met Gln Arg Leu Lys Thr Asn Ile
        755                 760                 765

Leu Gln Tyr Ala Ser Thr Arg Pro Pro Thr Leu Ser Pro Ile Pro His
    770                 775                 780

Ile Pro Arg Ser Pro Tyr Lys Phe Pro Ser Ser Pro Leu Arg Ile Pro
785                 790                 795                 800
```

```
Gly Gly Asn Ile Tyr Ile Ser Pro Leu Lys Ser Pro Tyr Lys Ile Ser
            805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
            835                 840                 845

Asn Gln Met Val Cys Asn Ser Asp Arg Val Leu Lys Arg Ser Ala Glu
        850                 855                 860

Gly Ser Asn Pro Pro Lys Pro Leu Lys Leu Arg Phe Asp Ile Glu
865                 870                 875                 880

Gly Ser Asp Glu Ala Asp Gly Ser Lys His Leu Pro Gly Glu Ser Lys
                885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
            915                 920                 925
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
ttctgtagtt taattttctg aacctttggc                                30

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
tcagccgaag agcttcagga agcaggg                                   27

<210> SEQ ID NO 11
<211> LENGTH: 32
<212> TYPE: PRT
<213> ORGANISM: Homo sapien
<220> FEATURE:
<221> NAME/KEY: VARIANT
<222> LOCATION: (2)..(3)
<220> FEATURE:
<221> NAME/KEY: VARIANT
<222> LOCATION: (6)..(13)
<220> FEATURE:
<221> NAME/KEY: VARIANT
<222> LOCATION: (15)
<220> FEATURE:
<221> NAME/KEY: VARIANT
<222> LOCATION: (17)..(18)
<220> FEATURE:
<221> NAME/KEY: VARIANT
<222> LOCATION: (20)..(21)
<220> FEATURE:
<221> NAME/KEY: VARIANT
<222> LOCATION: (23)..(28)
<220> FEATURE:
<221> NAME/KEY: VARIANT
<222> LOCATION: (30)..(31)

-continued

```
<400> SEQUENCE: 11

Cys Xaa Xaa Cys Xaa Xaa Xaa Xaa Xaa Xaa Xaa Xaa Cys Xaa His
 1               5                  10                  15

Xaa Xaa Cys Xaa Xaa Cys Xaa Xaa Xaa Xaa Xaa Cys Xaa Xaa Cys
            20                  25                  30

<210> SEQ ID NO 12
<211> LENGTH: 50
<212> TYPE: PRT
<213> ORGANISM: Homo sapien
<220> FEATURE:
<221> NAME/KEY: VARIANT
<222> LOCATION: (2)..(3)
<220> FEATURE:
<221> NAME/KEY: VARIANT
<222> LOCATION: (5)..(20)
<220> FEATURE:
<221> NAME/KEY: VARIANT
<222> LOCATION: (22)..(23)
<220> FEATURE:
<221> NAME/KEY: VARIANT
<222> LOCATION: (25)..(26)
<220> FEATURE:
<221> NAME/KEY: VARIANT
<222> LOCATION: (28)..(29)
<220> FEATURE:
<221> NAME/KEY: VARIANT
<222> LOCATION: (31)..(46)
<220> FEATURE:
<221> NAME/KEY: VARIANT
<222> LOCATION: (48)..(49)

<400> SEQUENCE: 12

Cys Xaa Xaa Cys Xaa Xaa Xaa Xaa Xaa Xaa Xaa Xaa Xaa Xaa Xaa
 1               5                  10                  15

Xaa Xaa Xaa Xaa His Xaa Xaa Cys Xaa Xaa Cys Xaa Cys Xaa Xaa
            20                  25                  30

Xaa Xaa Xaa Xaa Xaa Xaa Xaa Xaa Xaa Xaa Xaa Xaa Xaa Cys Xaa
            35                  40                  45

Xaa Cys
    50
```